(12) United States Patent
Atanasoska et al.

(10) Patent No.: US 8,895,099 B2
(45) Date of Patent: Nov. 25, 2014

(54) ENDOPROSTHESIS

(75) Inventors: Liliana Atanasoska, Edina, MN (US); Angela Kostrewa, Riverview, FL (US); Matthew Cambronne, Mounds View, MN (US); James Q. Feng, Maple Grove, MN (US); Rajesh Radhakrishnan, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 491 days.

(21) Appl. No.: 13/051,558

(22) Filed: Mar. 18, 2011

(65) Prior Publication Data

US 2011/0238149 A1 Sep. 29, 2011

Related U.S. Application Data

(60) Provisional application No. 61/317,830, filed on Mar. 26, 2010.

(51) Int. Cl.
| | |
|---|---|
| *B05D 3/00* | (2006.01) |
| *A61L 33/00* | (2006.01) |
| *A61F 2/06* | (2013.01) |
| *A61L 31/16* | (2006.01) |
| *A61L 31/06* | (2006.01) |
| *A61L 31/14* | (2006.01) |
| *A61L 31/08* | (2006.01) |
| *A61L 31/10* | (2006.01) |
| *A61L 31/02* | (2006.01) |

(52) U.S. Cl.
CPC ............... *A61L 31/022* (2013.01); *A61L 31/16* (2013.01); *A61L 31/06* (2013.01); *A61L 31/148* (2013.01); *A61L 31/088* (2013.01); *A61L 31/10* (2013.01)
USPC ....... 427/2.24; 427/2.25; 623/1.39; 623/1.15; 623/1.42

(58) Field of Classification Search
CPC ............ A61L 31/10; A61L 31/16; A61F 2/06
USPC .......................................................... 427/2.1
See application file for complete search history.

(56) References Cited

U.S. PATENT DOCUMENTS

| | | | |
|---|---|---|---|
| 6,290,721 B1 | 9/2001 | Heath | |
| 7,955,382 B2 * | 6/2011 | Flanagan et al. ............. | 623/1.42 |

(Continued)

FOREIGN PATENT DOCUMENTS

| | | | |
|---|---|---|---|
| WO | WO2008134493 | 11/2008 | |
| WO | WO 2008134493 A1 * | 11/2008 | ................ A61F 2/90 |

(Continued)

OTHER PUBLICATIONS

International Preliminary Report on Patentability issued on Oct. 11, 2012 in PCT application No. PCT/US2011/029005, filed Mar. 18, 2011.

(Continued)

*Primary Examiner* — Dah-Wei D Yuan
*Assistant Examiner* — Hai Yan Zhang
(74) *Attorney, Agent, or Firm* — Fish & Richardson P.C.

(57) ABSTRACT

Endoprostheses and methods of making endoprostheses are disclosed. For example, endoprostheses are described that include an endoprosthesis body, a biodegradable metallic tie layer, and a polymer coating about the endoprosthesis body. The biodegradable tie layer and the polymer coating can have a high peel strength from the body.

15 Claims, 23 Drawing Sheets

(56) References Cited

U.S. PATENT DOCUMENTS

| | | | |
|---|---|---|---|
| 2002/0144757 A1 | 10/2002 | Craig et al. | |
| 2003/0018380 A1 | 1/2003 | Craig et al. | |
| 2003/0077200 A1 | 4/2003 | Craig et al. | |
| 2004/0073284 A1* | 4/2004 | Bates et al. | 623/1.11 |
| 2004/0143317 A1 | 7/2004 | Stinson et al. | |
| 2004/0254608 A1* | 12/2004 | Huitema et al. | 606/219 |
| 2005/0019265 A1 | 1/2005 | Hammer et al. | |
| 2005/0025804 A1* | 2/2005 | Heller | 424/423 |
| 2005/0070990 A1 | 3/2005 | Stinson | |
| 2005/0216074 A1 | 9/2005 | Sahatjian et al. | |
| 2005/0234545 A1* | 10/2005 | Su et al. | 623/1.46 |
| 2005/0251249 A1* | 11/2005 | Sahatjian et al. | 623/1.46 |
| 2006/0029720 A1* | 2/2006 | Panos et al. | 427/2.1 |
| 2006/0153729 A1 | 7/2006 | Stinson et al. | |
| 2006/0229711 A1* | 10/2006 | Yan et al. | 623/1.38 |
| 2006/0259033 A1* | 11/2006 | Nesbitt | 606/45 |
| 2007/0224244 A1* | 9/2007 | Weber et al. | 424/424 |
| 2007/0237800 A1* | 10/2007 | Lahann | 424/422 |
| 2007/0260054 A1* | 11/2007 | Chudzik | 536/123.12 |
| 2007/0270942 A1* | 11/2007 | Thomas | 623/1.46 |
| 2008/0057105 A1* | 3/2008 | Atanasoska et al. | 424/426 |
| 2008/0071351 A1* | 3/2008 | Flanagan et al. | 623/1.15 |
| 2008/0082162 A1* | 4/2008 | Boismier et al. | 623/1.38 |
| 2008/0086195 A1* | 4/2008 | Atanasoka et al. | 623/1.15 |
| 2008/0131479 A1* | 6/2008 | Weber et al. | 424/426 |
| 2008/0147177 A1* | 6/2008 | Scheuermann et al. | 623/1.42 |
| 2008/0294236 A1 | 11/2008 | Anand et al. | |
| 2008/0294246 A1* | 11/2008 | Scheuermann et al. | 623/1.49 |
| 2009/0024211 A1* | 1/2009 | Wittchow | 623/1.45 |
| 2009/0030500 A1* | 1/2009 | Weber et al. | 623/1.15 |
| 2009/0053392 A1* | 2/2009 | Kramer-Brown et al. | 427/2.24 |
| 2009/0081313 A1* | 3/2009 | Aghion et al. | 424/641 |
| 2009/0281613 A1* | 11/2009 | Atanasoska et al. | 623/1.15 |
| 2009/0319032 A1* | 12/2009 | Weber et al. | 623/1.39 |
| 2010/0076556 A1* | 3/2010 | Tomantschger et al. | 623/11.11 |
| 2010/0137971 A1* | 6/2010 | Lootz et al. | 623/1.15 |
| 2010/0272882 A1 | 10/2010 | Radhakrishnan et al. | |
| 2010/0324666 A1* | 12/2010 | Klocke et al. | 623/1.44 |

FOREIGN PATENT DOCUMENTS

| | | | |
|---|---|---|---|
| WO | WO2009137786 | 11/2009 | |
| WO | WO 2009137786 A1 * | 11/2009 | A61F 2/90 |

OTHER PUBLICATIONS

Antunes et al., "Characterization of Corrosion Products Formed on Steels in the First Months of Atmospheric Exposure", Materia, vol. 8, No. 1, pp. 27-34, (2003).

Buster et al., "Crystal habits of the Magnesium Hydroxide mineral Brucite within Coral Skeletons," American Geophysical Union Annual Meeting, Abstract and Poster, pp. 1-3, (2006).

Guo et al., "Investigation of corrosion behaviors of Mg-6Gd-3Y-0.4Zr alloy in NaCl aqueous solutions," Electrochimica Acta, vol. 52, pp. 2570-2579, (2007).

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

International Search Report and Written Opinion issued on Jun. 28, 2011 in PCT application No. PCT/US2011/029005, filed on Mar. 18, 2011.

Kogure et al., "Microstructure of nemalite, fibrous iron-bearing brucite", Mineralogical Journal, vol. 20, No. 3, pp. 127-133, Jul. 1998.

Lee et al., "A study on electrophoretic deposition of Ni nanoparticles on pitted Ni alloy 600 with surface fractality", Journal of Colloid and Interface Science, vol. 308, pp. 413-420, (2007).

Li et al., "A novel method for preparing surface-modified Mg(OH)2 nanocrystallines," Materials Science and Engineering A, 452-453, pp. 302-305, (2007).

Liebling et al., "Optical Properties of Fibrous Brucite from Asbestos, Quebec", American Mineralogist, vol. 57, pp. 857-864, (1972).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces A: Physicochemical and Engineering Aspects, vol. 296, pp. 97-103, (2007).

Matijević, "Colloid Chemical Aspects of Corrosion of Metals", Pure & Applied Chemisty, vol. 52, pp. 1179-1193, (1980).

Mobedi et al., "Studying the Degradation of Poly(L-lactide) in Presence of Magnesium Hydroxide", Iranian Polymer Journal, vol. 15, No. 1, pp. 31-39, (2006).

Nair et al., "Biodegradable polymers as biomaterials", Progress in Polymer Science, vol. 32, pp. 732-798, (2007).

Park et al., "Cathodic electrodeposition of $RuO_2$ thin films from Ru(III)C13 solution", Materials Chemistry and Physics, vol. 87, pp. 59-66, (2004).

Qiu et al., "Self-assembled growth of MgO nanosheet arrays via a micro-arc oxidations technique," Applied Surface Science vol. 253, pp. 3987-3990, (2007).

Robbie et al., "Advanced techniques for glancing angle deposition," Journal of Vacuum Science and Technology B, vol. 16, No. 3, pp. 1115-1122, (May/Jun. 1998).

Schetsky, "Shape Memory Alloys", Encyclopedia of Chemical Technology (3rd ed.), John Wiley & Sons, vol. 20, pp. 726-736, (1982).

Shibli et al., "Development of phosphate inter layered hydroxyapatite coating for stainless steel implants", Applied Surface Science, vol. 254, pp. 4103-4110, (2008).

Studart et al., "Colloidal Stabilization of Nanoparticles in Concentrated Suspensions," Langmuir, vol. 23, pp. 1081-1090, (2007).

Yang et al., "Solution phase synthesis of magnesium hydroxide sulfate hydrate nanoribbons", Nanotechology, vol. 15, pp. 1625-1627, (2004).

Zhang et al., "Surface treatment of magnesium hydroxide to improve its dispersion in organic phase by the ultrasonic technique", Applied Surface Science, vol. 253, pp. 7393-7397, (2007).

Zou et al., "Highly textural lamellar mesostructured magnesium hydroxide via a cathodic electrodeposition process", Materials Letters, vol. 61, pp. 1990-1993, (2007).

\* cited by examiner

EHT = 1.00 kV   Signal A = SE2   Chamber = 7.60e-004 Pa
200nm*   Mag = 20.00 KX   WD = 4mm EHT = 1.00 kV   Signal A = SE2   Chamber = 3.70e-004 Pa
200nm*   Mag = 1.00 KX   WD = 4mm Hematite -$Fe_2O_3$ platelet structure Lepidocrocite γ-FeOOH structure
(fine plates flowery structure)

Lepidocrocite -FeOOH structure
(fine plates flowery structure)

Lepidocrocite -FeOOH structure (fine plates flowery structure)

Lepidocrocite -FeOOH structure (sandy crystals)

US 8,895,099 B2

ENDOPROSTHESIS

CROSS-REFERENCE TO RELATED APPLICATION

This application claims priority under 35 USC §119(e) to U.S. Provisional Patent Application Ser. No. 61/317,830, filed on Mar. 26, 2010, the entire contents of which are hereby incorporated by reference.

TECHNICAL FIELD

This invention relates to endoprosthesis.

BACKGROUND

The body includes various passageways such as arteries, other blood vessels and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In an aspect, the invention features an endoprosthesis including a metallic biodegradable material having a surface morphology substantially including features having thickness to width ratio of about 8 to 1 or more.

In an aspect, the invention features a method of forming an endorprosthesis, including providing a biodegradable material having a select morphology by controlling corrosion of a metal, and utilizing the corroded metallic material in the endorprosthesis.

In an aspect, the invention features a method of forming an endoprosthesis including providing a biodegradable material having a select morphology by depositing a metallic material by GLAD.

Embodiments and/or aspects may include any one or more of the following advantages. Endoprostheses can be provided to have enhanced adhesion of a polymer coating to a stent body through one of more tie layers between the polymer coating and the stent body. A first tie layer including a material such as magnesium, iron, or magnesium hydroxide, can be formed on the stent body made of, e.g. a metallic material such as stainless steel, to have a high roughness morphology, such as rice grain or corn flake. The high roughness morphology of the first tie layer can mechanically interlock the polymer coating with a greatly enhanced adhesion. Optionally, a second tie layer including a polymer can be formed between the first tie layer and the polymer coating, and further enhances the adhesion of the polymer coating to the stent body. The second tie layer can bind to the first tie layer through mechanical interlocking and chemical bonding, and the polymer coating can bind to the second tie layer through chemical bonding. The first and second tie layers and the polymer coating can be biodegradable. The polymer coating can contain a therapeutic agent so that the endoprosthesis can deliver a drug. When the endoprosthesis is delivered to a body or body lumen, the therapeutic agent is released, and the first tie layer, the second tie layer, and the polymer coating degrades over time, so that the stent body remains in the body or body lumen without overcoatings. The stent body surface made of a metallic material, such as stainless steel, can promote endolithium prohealings.

Other features, objects, and advantages of the invention are in the claims.

DETAILED DESCRIPTION

Figure 1A:
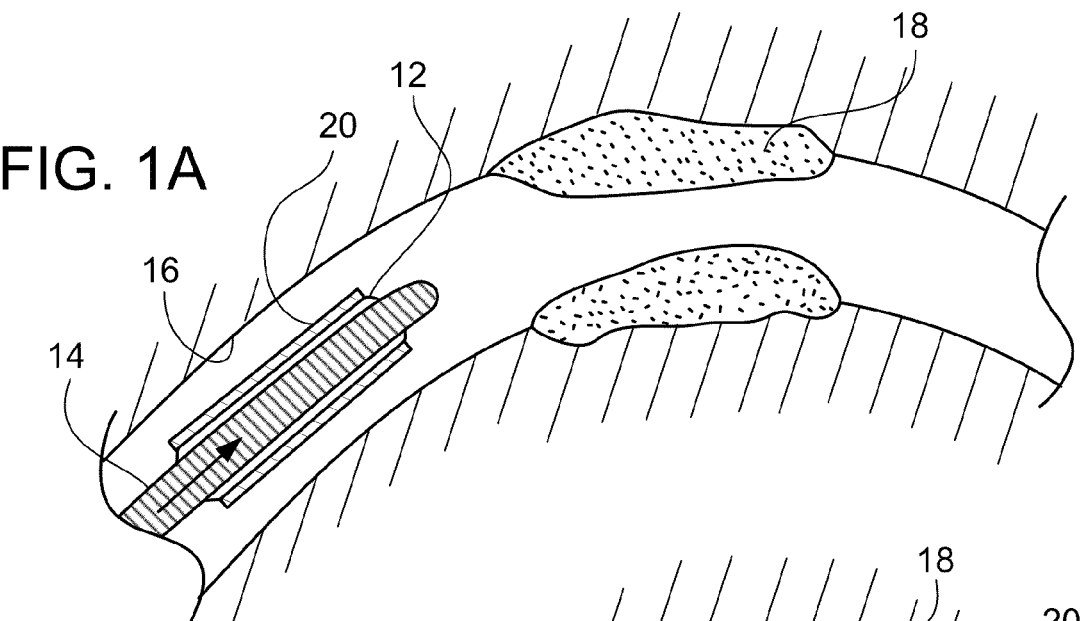
FIGS. 1A-1C are longitudinal cross-sectional views, illustrating delivery of a stent in a collapsed state, expansion of the stent, and deployment of the stent.
Figure 1B:
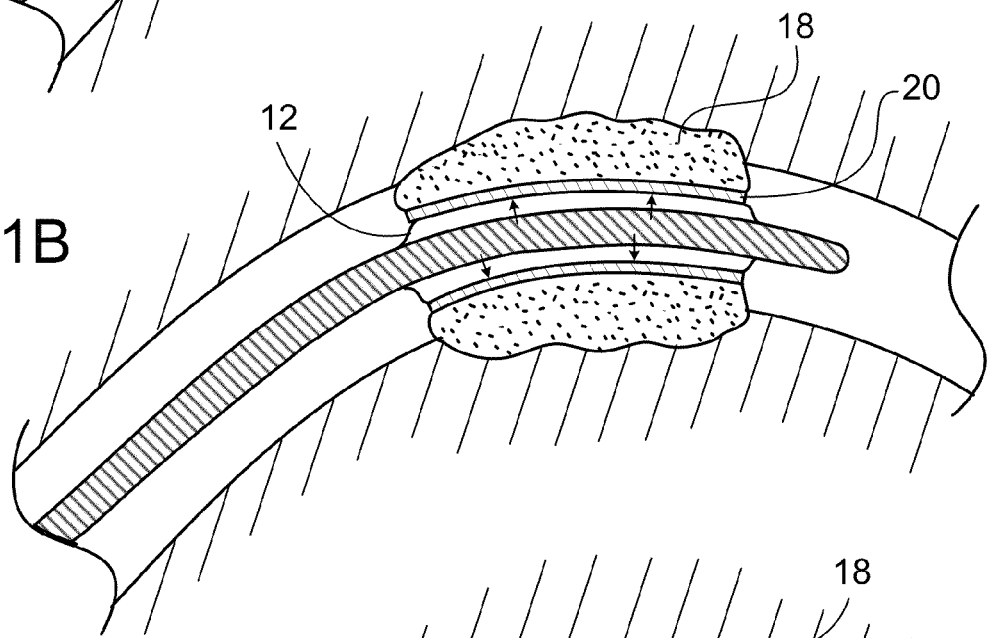
Figure 1C:
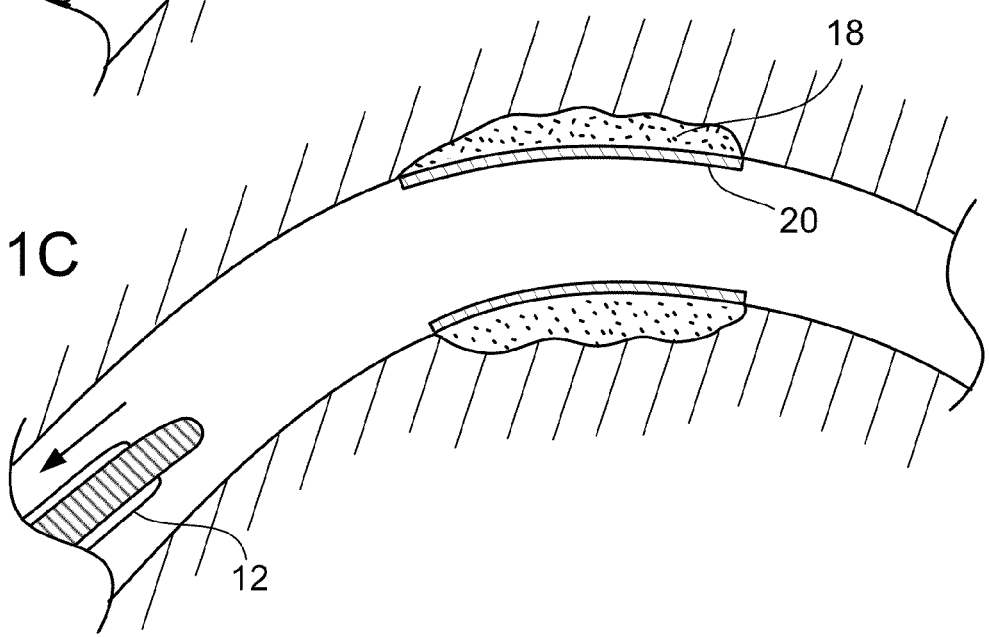

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
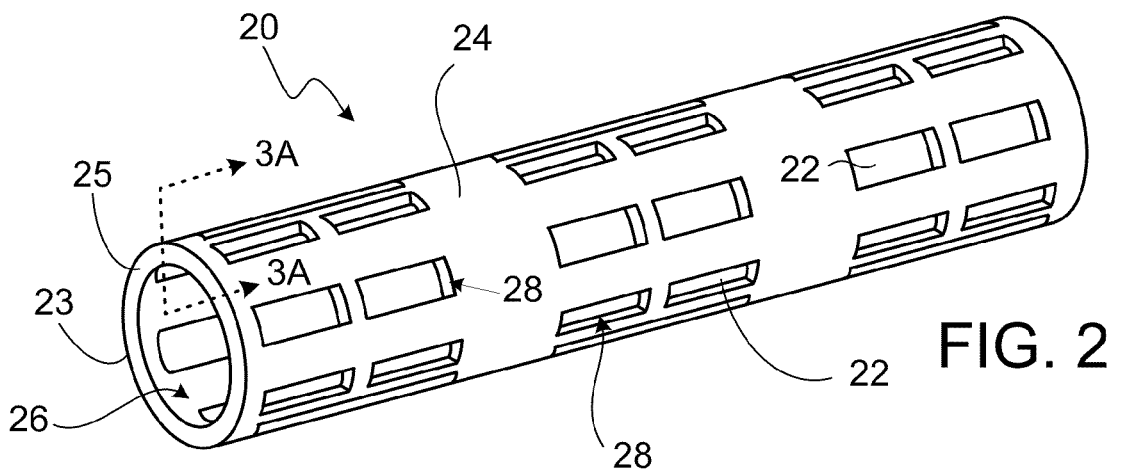
FIG. 2 is a perspective view of a fenestrated stent.

Referring to FIG. 2, stent 20 includes a plurality of fenestrations 22 defined in a wall 23. Stent 20 includes several surface regions, including an outer, or abluminal, surface 24, an inner, adluminal, surface 26, and a plurality of cutface surfaces 28. The stent can be balloon expandable, as illustrated above, or a self-expanding stent. Examples of stents are described in Heath '721, supra.

Figure 3A:
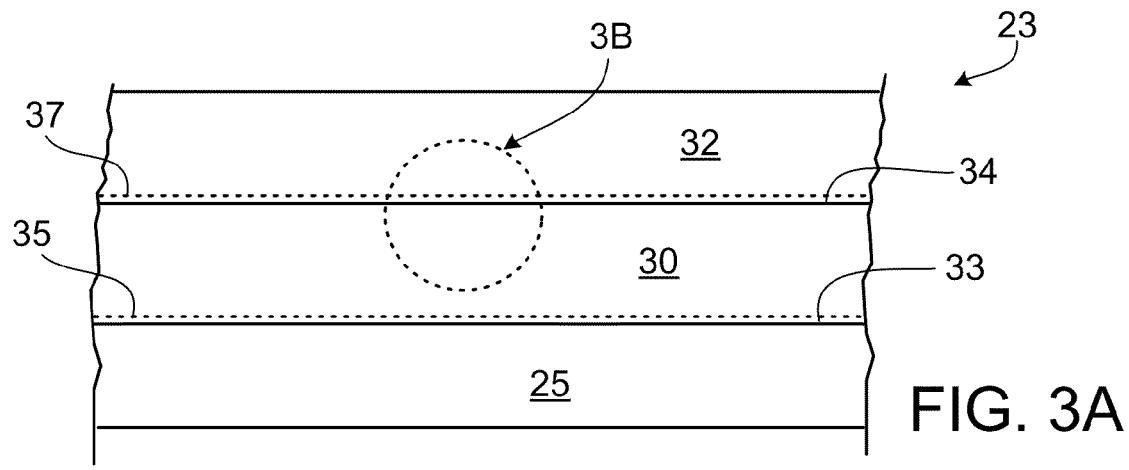
FIG. 3A is a cross-sectional view of a stent wall.
Figure 3B:
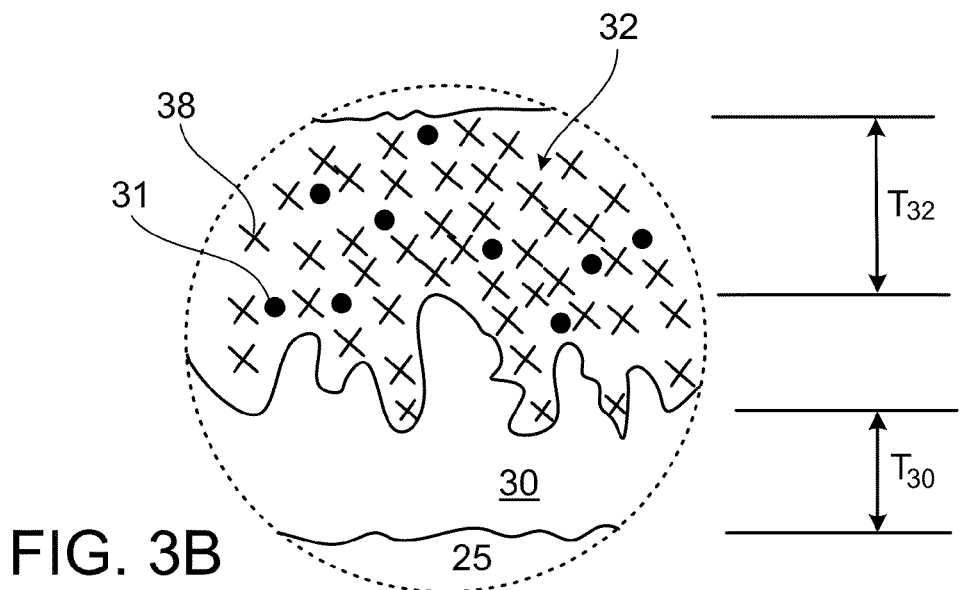
FIG. 3B is a greatly enlarged cross-sectional view of a part of the stent wall of FIG. 3A.

Referring to FIGS. 3A and 3B, a stent wall 23 includes a stent body 25, on which is provided a biodegradable metallic or ceramic tie layer 30, e.g., magnesium oxide, on, e.g., the abluminal side of the stent body. A second coating 32, such as a biodegradable polymeric material that includes a drug 31 dispersed thereon and/or therein, is provided over the tie layer. In use, after implantation in the body, drug is released from the polymeric coating 32 and the coating 32 degrades, exposing a surface 34 of the tie layer 30. The biodegradable tie layer 30 also degrades as it is exposed to body fluid, particularly by degradation of the overlying coating 32. After the biodegradable tie layer 30 substantially degrades, the surface 33 of the stent body is exposed to tissue. The surface 33 of the stent body can be a selected material (e.g. stainless steel) and/or treated (e.g. to have a desired morphology) to enhance healing, e.g., by promoting endothelialization. In embodiments, a further coating 35 (dotted), e.g. a substantially nondegradable ceramic such as IROX with a select morphology can be provided over the stent body to, e.g., promote endothelialization. In embodiments, a coating 37 with selected properties such as hydrophobicity/hydrophilicity or the ability to covalently bond can be provided over the tie layer 30 to further enhance adhesion of the polymer coating 32.

The polymer coating 32 is bonded to the tie layer 30 at an interface region at which the tie layer 30 has a selected morphology. The morphology is tuned to a desired shape, roughness, and chemistry to adjust the binding of the polymer coating to the tie layer and the degradation rate of the tie layer. For example, a high surface area morphology can enhance the bonding between the polymer and the tie layer, thus reducing the likelihood of delamination of the polymer layer. A more porous morphology can increase the rate of degradation of the tie layer.

Figure 4A:
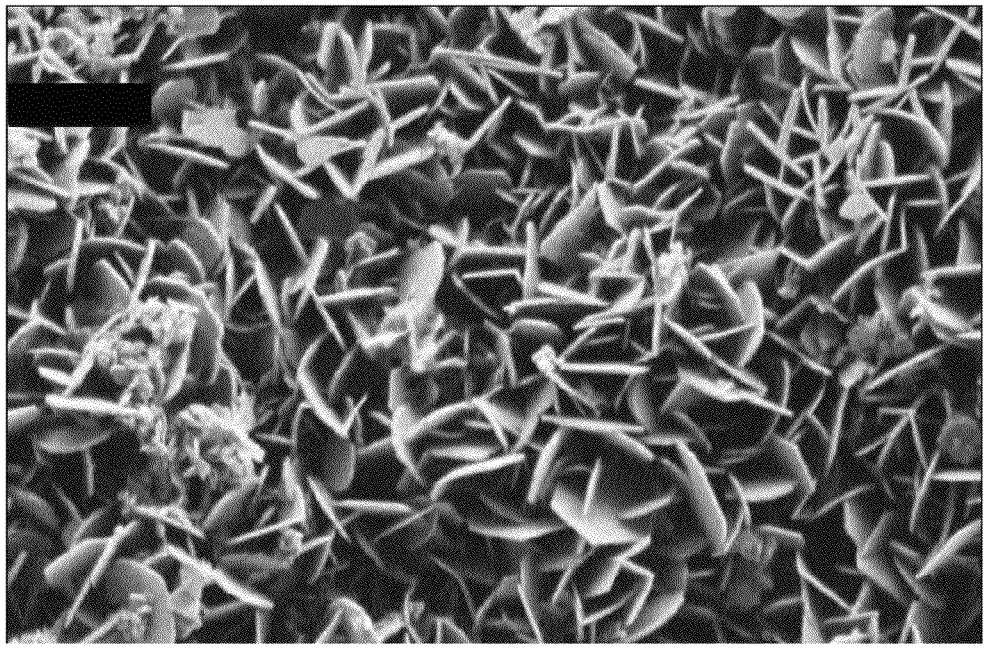
FIGS. 4A-4H are SEM images of different morphologies.
Figure 4B:
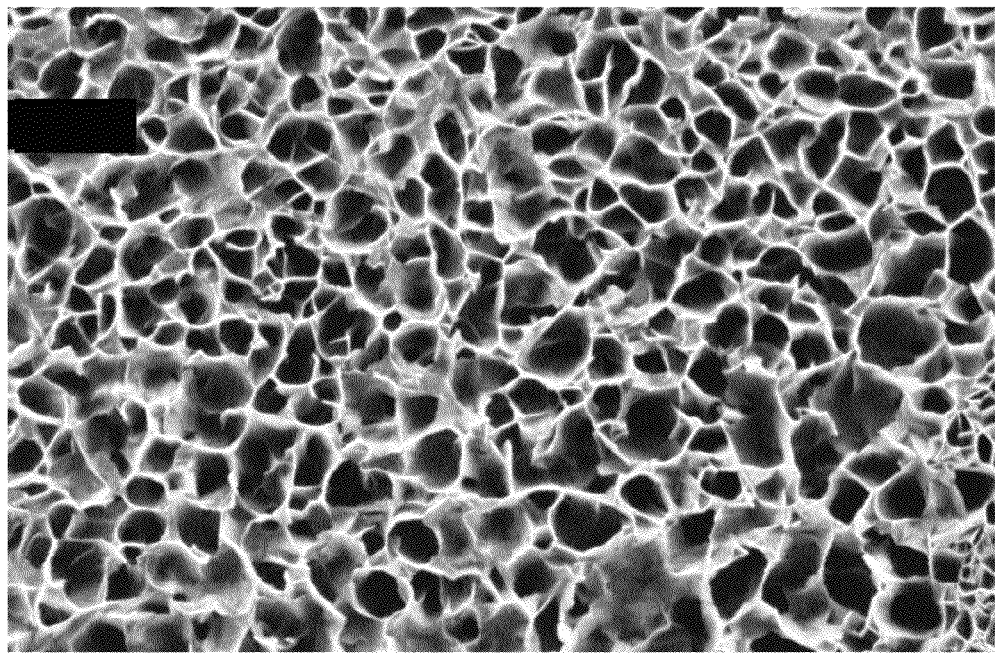
Figure 4C:
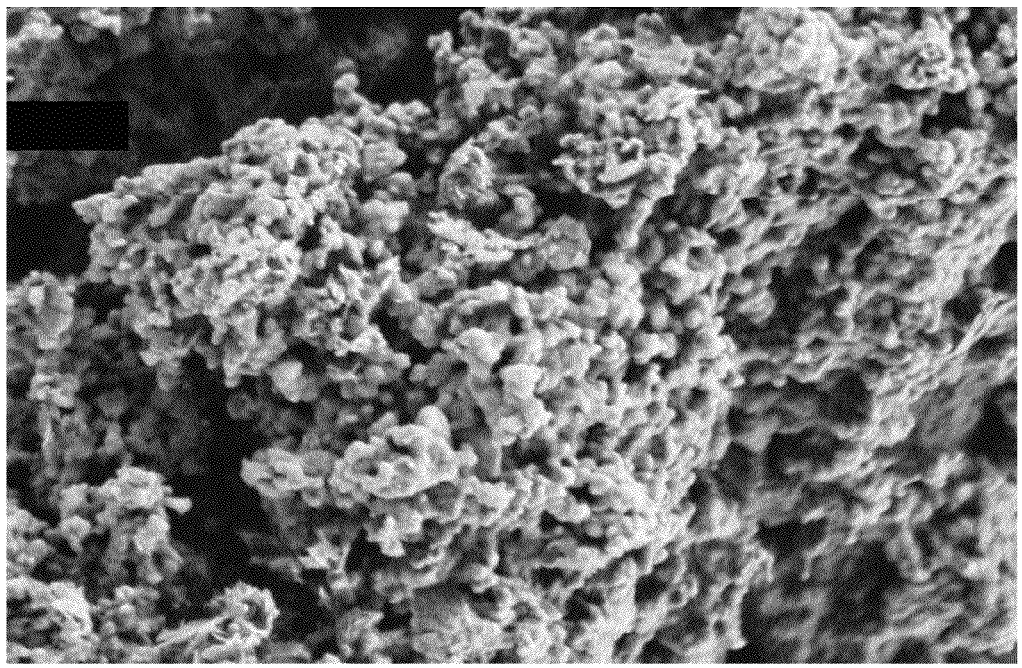
Figure 4D:
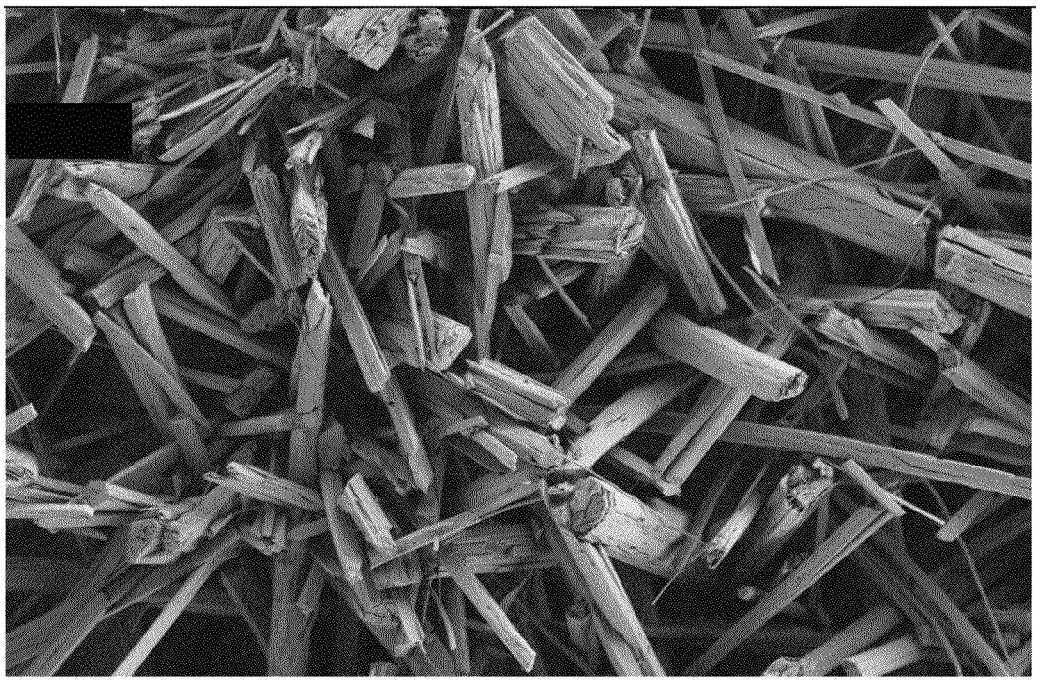
Figure 4E:
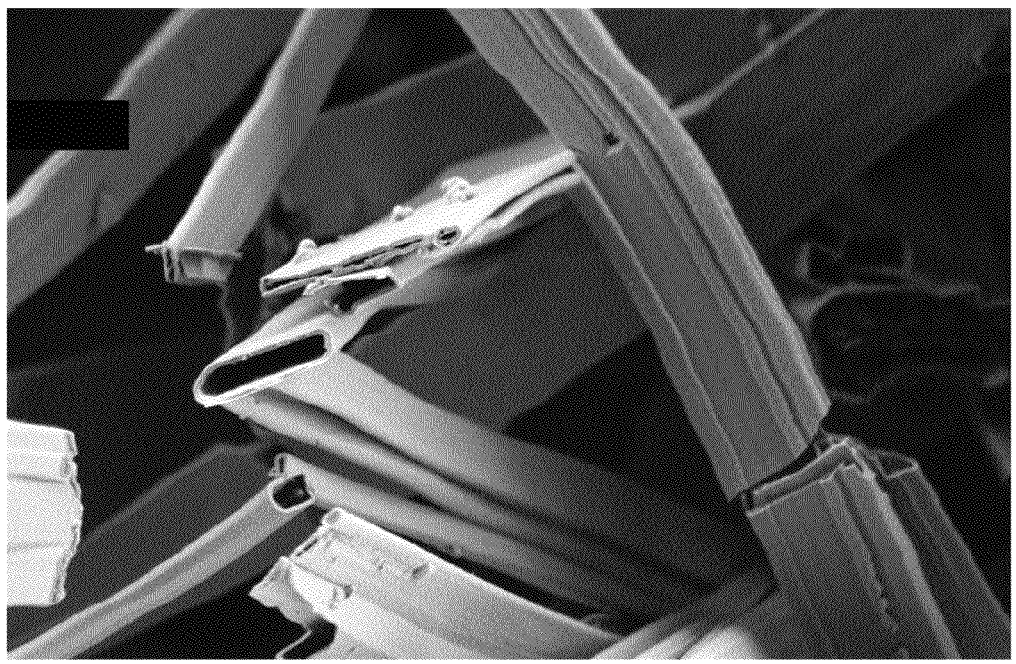
Figure 4F:
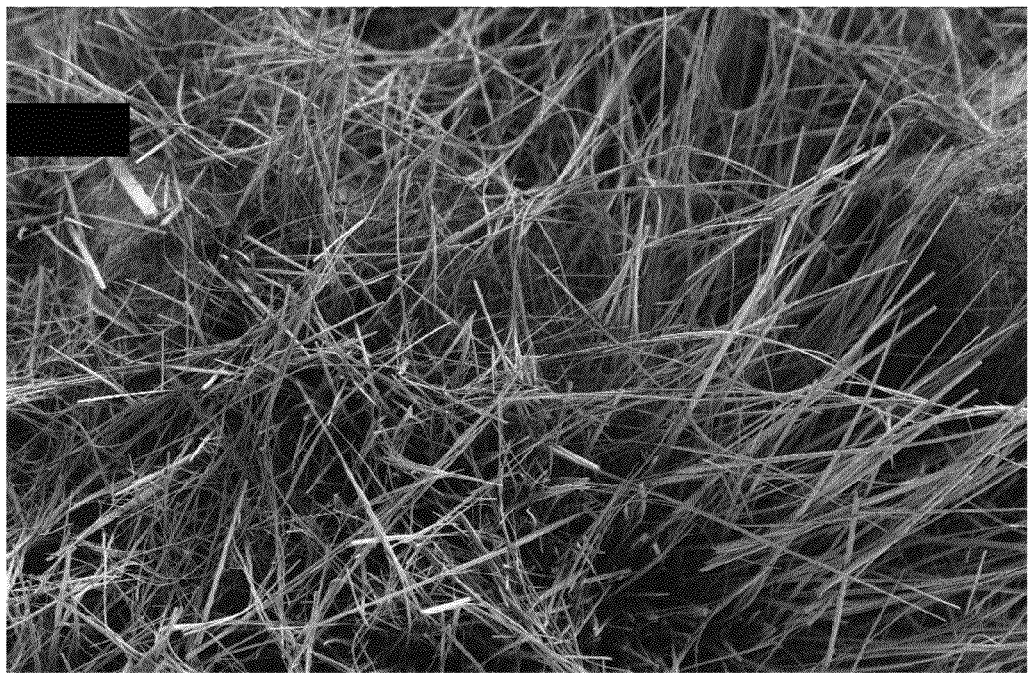
Figure 4G:
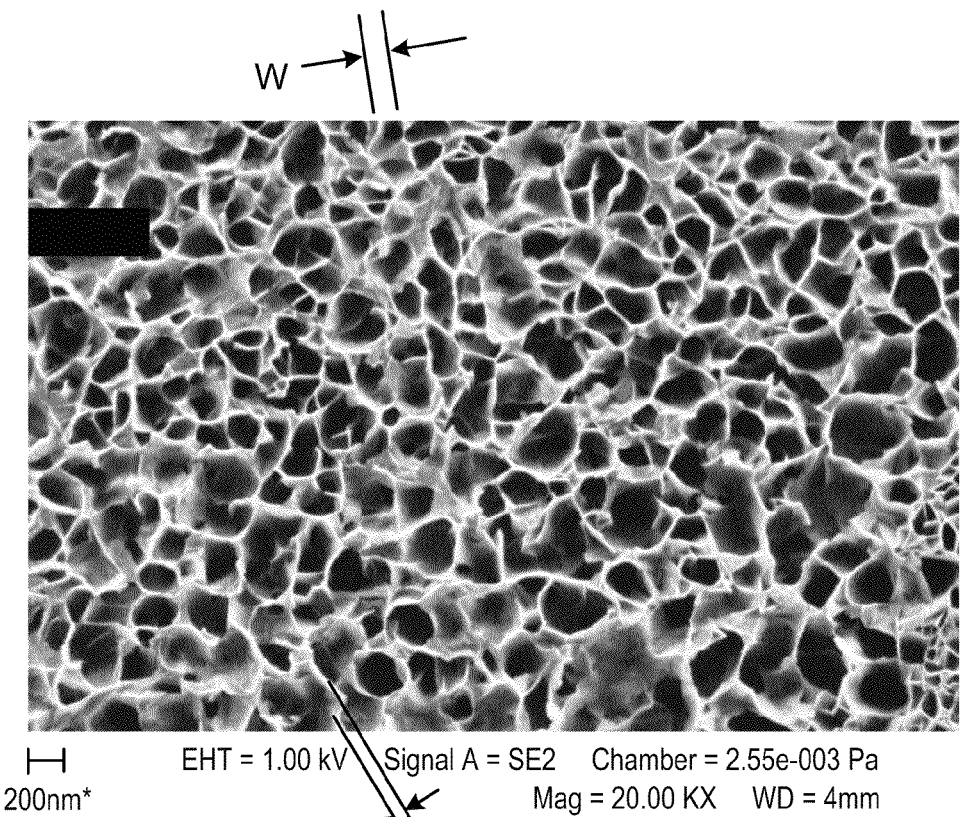
Figure 4H:
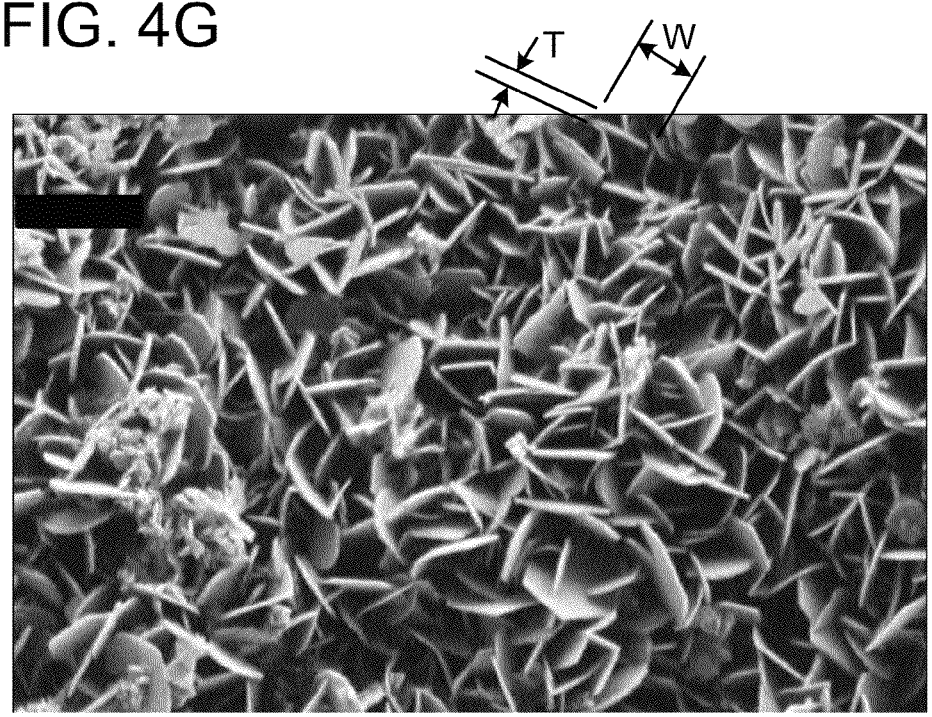

Referring to FIGS. 4A-4H, eight exemplary nano-structured morphologies of a biodegradable material, such as magnesium oxide are shown. Referring particularly to FIG. 4A, the material can have a morphology characterized by defined rice grains and high roughness. Referring particularly to FIG. 4B, the material can have a morphology characterized by defined cornflakes. Referring particularly to FIG. 4C, the material can have a morphology characterized by defined cauliflowers. Referring particularly to FIG. 4D, the material can have a morphology characterized by defined nano-rods. Referring particularly to FIG. 4E, the material can have a defined nano-ribbon morphology. Referring to FIG. 4F, the material can have a morphology characterized by defined nano-needles. Referring to FIG. 4G, a cornflake type morphology is characterized by a highly porous surface defined by interconnecting flakes. In embodiments, ratio of the pore width (w) to flake thickness (T) is about 10 to 1 or greater, e.g. 20 to 1 or greater. In embodiments, thickness of the flakes is about 20 nm or less, e.g. 10 nm or less and the width of the pores is about 50 nm or more, e.g. 100 nm or more. Referring to FIG. 4H, a rice grain type morphology is characterized by substantially discrete, relatively wide, thin features having, in embodiments, a width (W) to thickness (T) ratio of about 8 to 1 or greater, e.g. 15 to 1 or greater. In embodiments, the thickness is about 30 nm to less, e.g. about 15 nm or less and the width is about 100 nm or more, e.g. about 200 nm or more.

The morphologies can be formed by exposing a metal, e.g., magnesium, to a corrosive environment, e.g., by immersing in an electrolyte such as NaCl solution which will corrode magnesium by a chloride and/or galvanic effect. For example, a uniform coating is formed on the stent body by depositing, e.g., a magnesium alloy such as Mg—Gd—Y—Zr alloy, using physical vapor deposition, vacuum evaporation, or electrodeposition. In embodiments, magnesium ion implantation can also used to form the uniform coating. In such embodiments, because of the high energy of the implanting magnesium ions, an intermix layer made of magnesium and the stent body material is formed between the stent body and the uniform magnesium coating. The intermix layer can enhance adhesion between the magnesium alloy coating and the stent body.

Figure 5A:
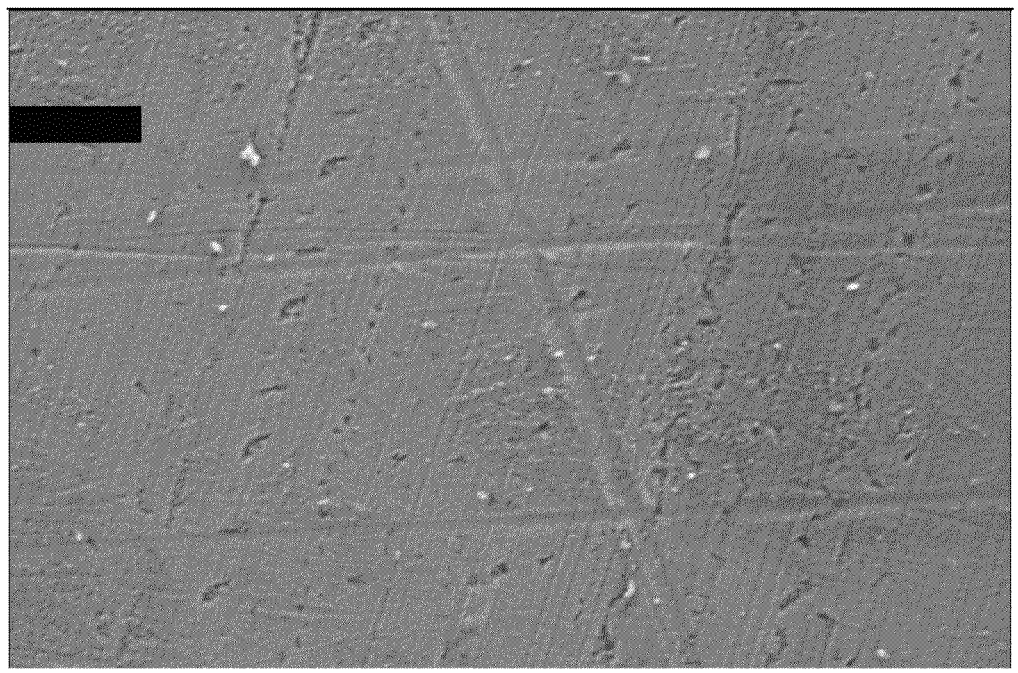
FIGS. 5A-5C are SEM images.
Figure 5B:
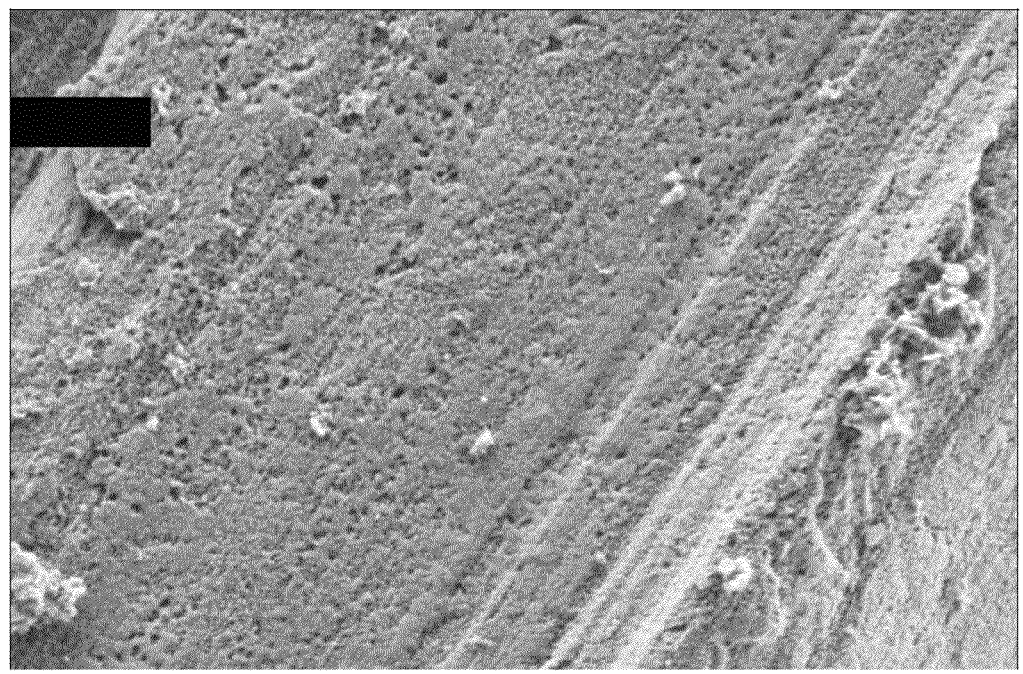
Figure 5C:
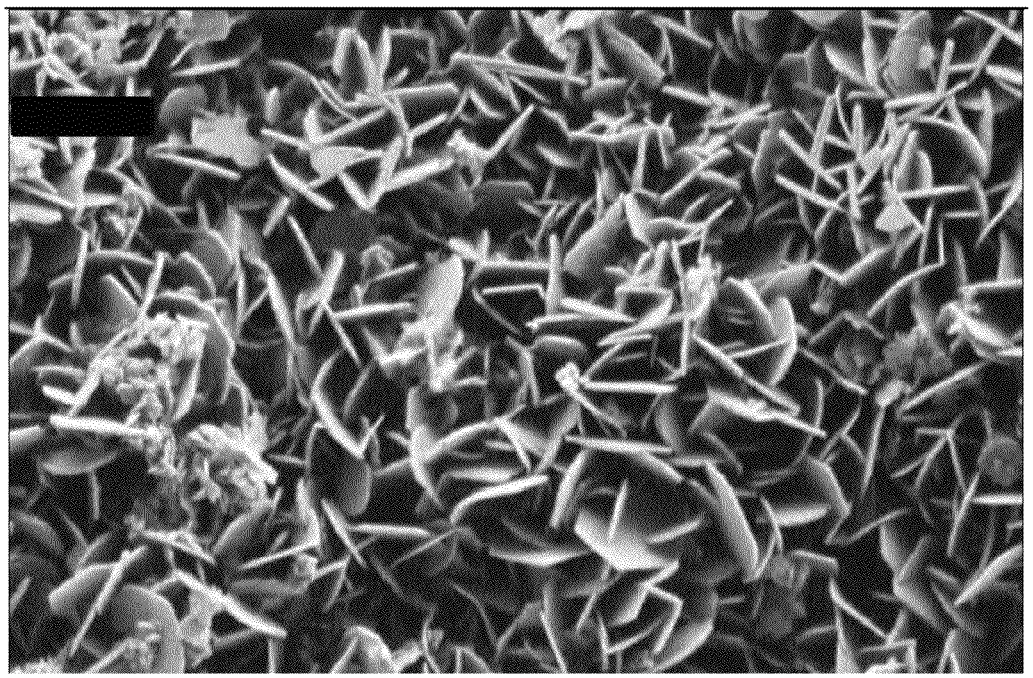
Figure 6A:
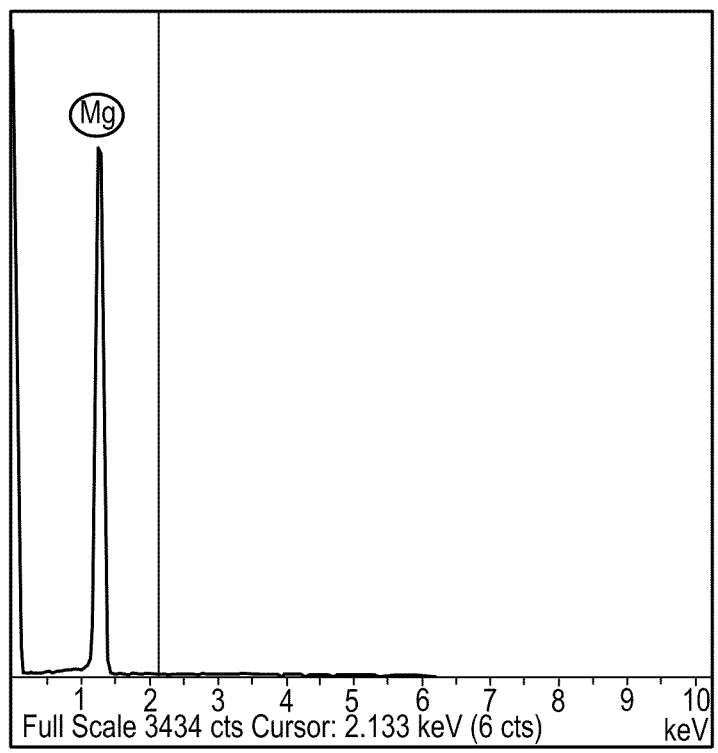
FIGS. 6A-6C are EDX plots.
Figure 6B:
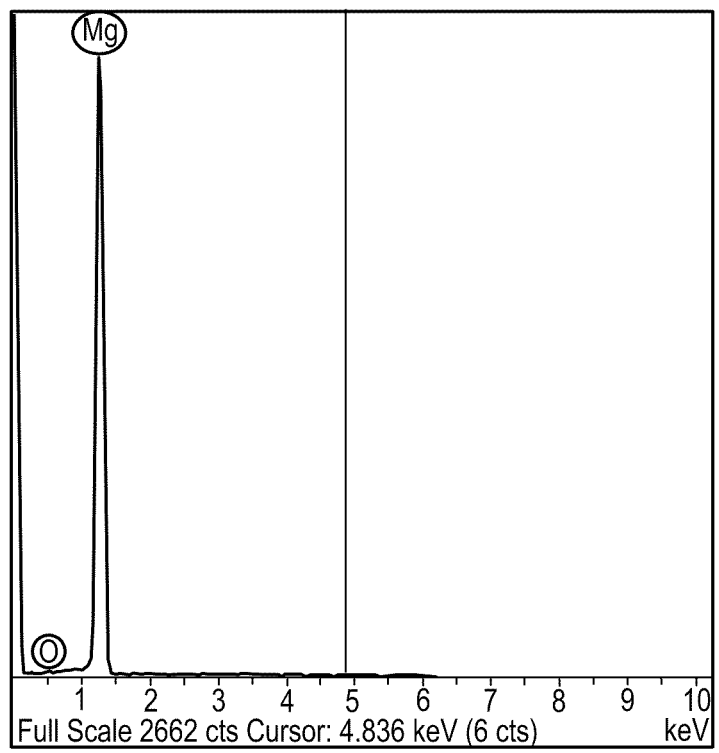
Figure 6C:
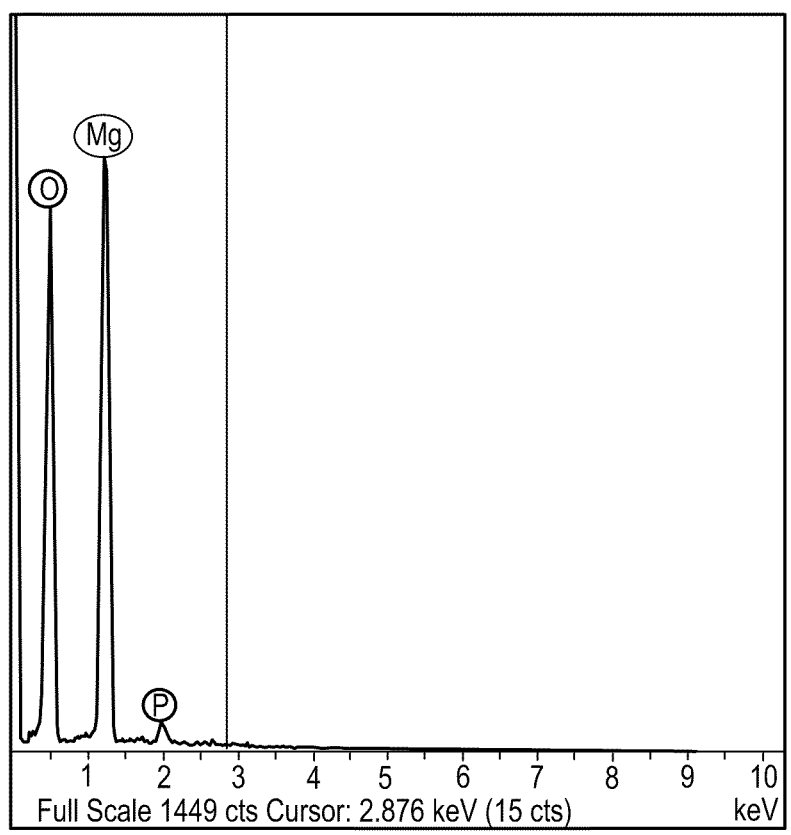

Rice grain and cornflake morphologies are formed by exposure to an environment that will induce and accelerate corrosion such as an NaCl solution. Referring to FIGS. 5A-5C, SEM images are provided of a polished magnesium surface, the surface after initial corrosion, and the surface after substantial conversion showing a rice grain morphology. Referring to FIGS. 6A-6C, corresponding EDX images are provided. The rice grain morphology in FIGS. 5C and 6C is formed after 24 hours of immersion in 0.9% PBS (phosphate buffered saline) solution. The roughness of the magnesium hydroxide can be tailored by controlling the conditions of corrosion. For example, under the same conditions, a longer immersion time produces a rice grain morphology, while a shorter immersion time produces a corn flake morphology. In some embodiments, when the coating includes a magnesium hydroxide, surface morphologies, e.g., rice grain or cornflakes, can be obtained by anodization or immersion of the coating.

Figure 7A:
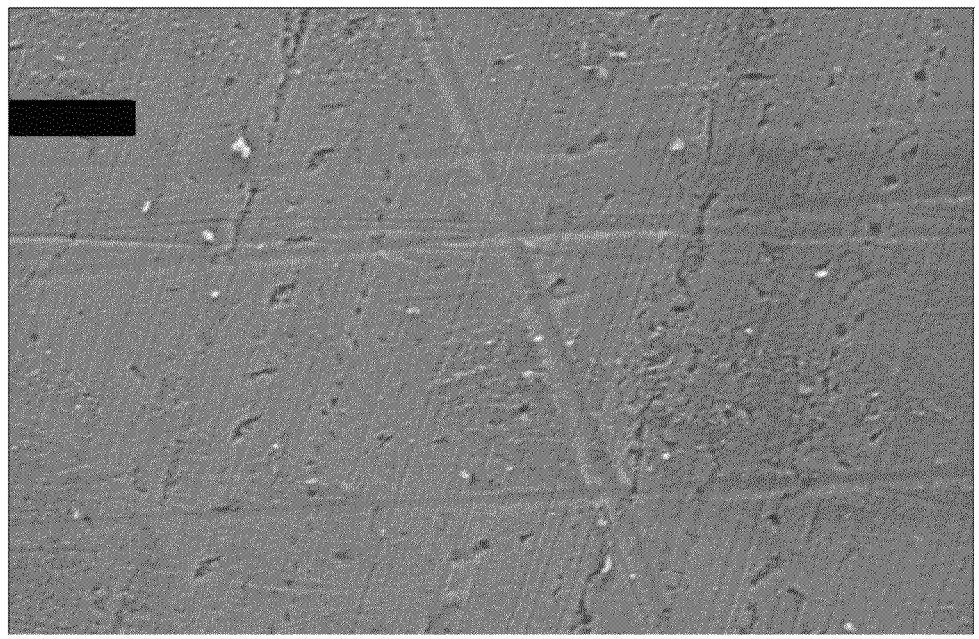
FIGS. 7A-7C are SEM images.
Figure 7B:
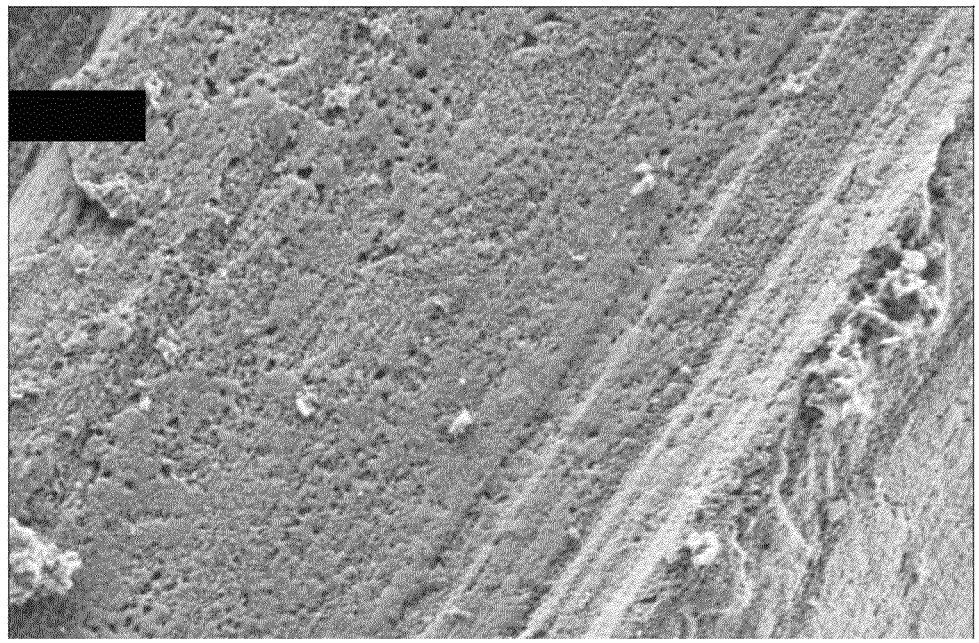
Figure 7C:
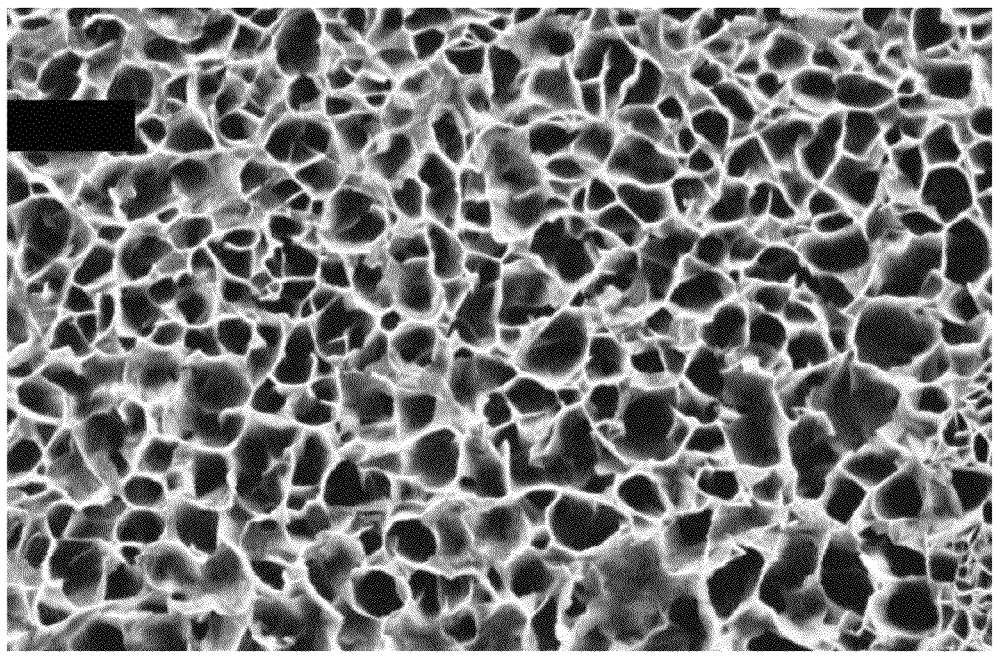
Figure 8A:
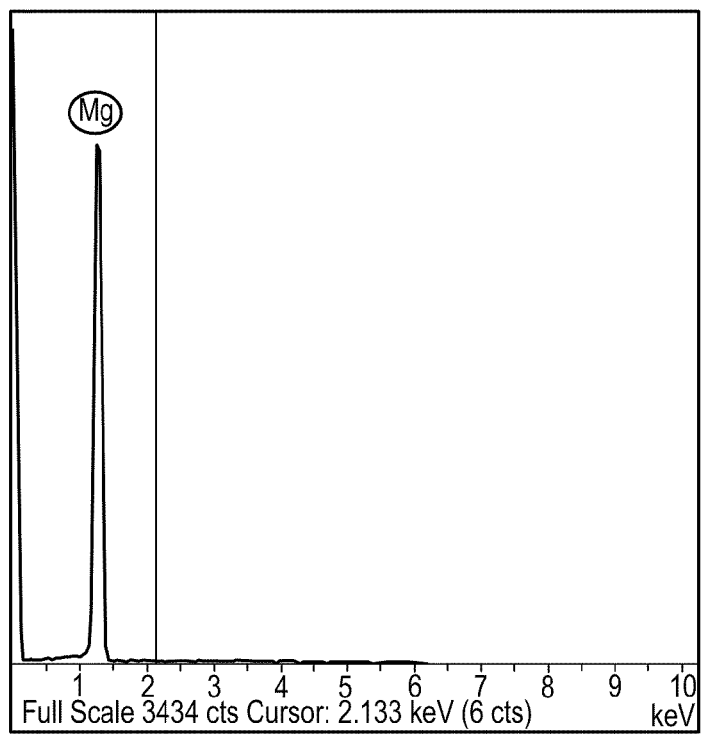
FIGS. 8A-8C are EDX plots.
Figure 8B:
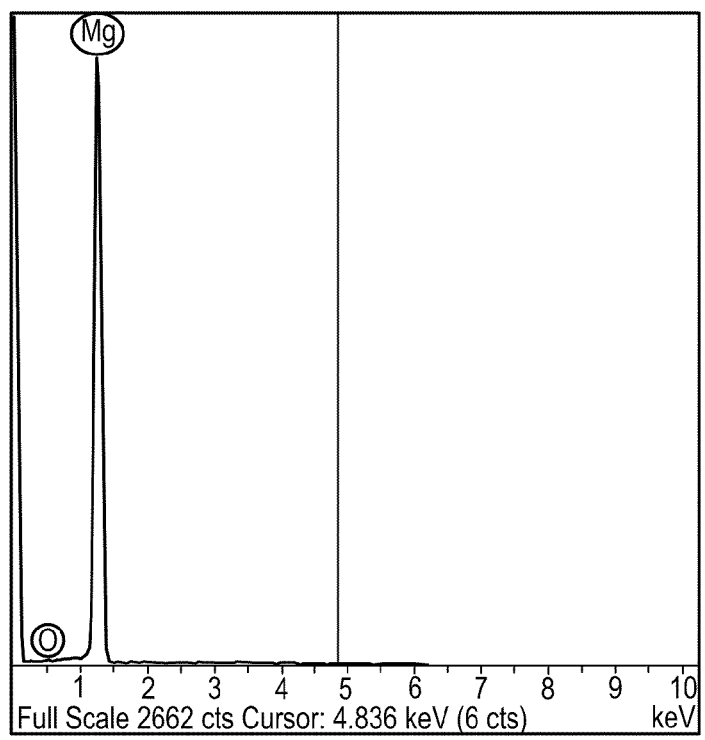
Figure 8C:
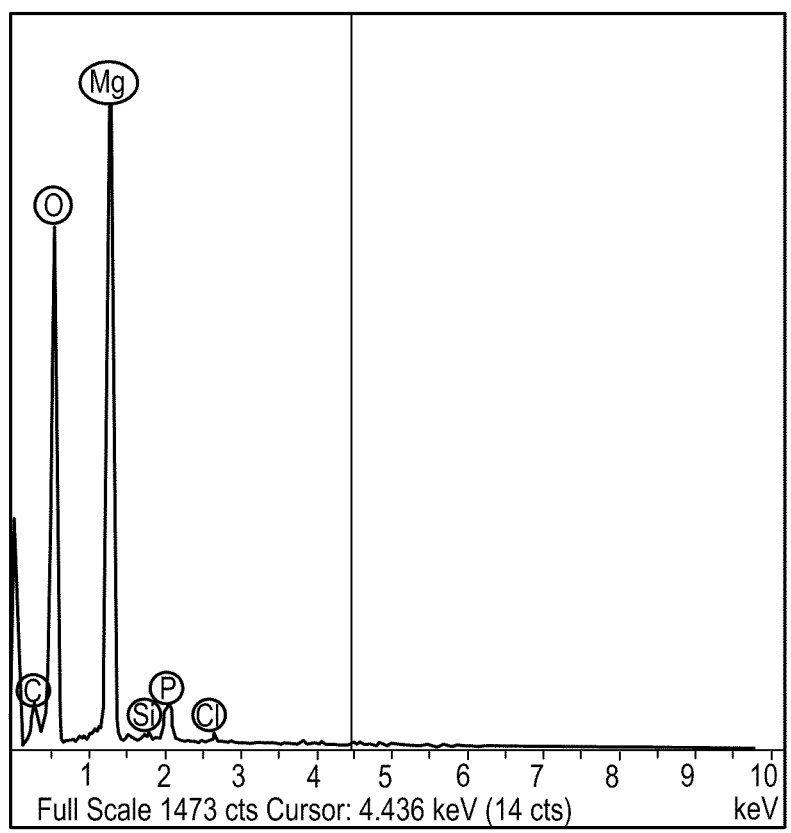

Referring to FIGS. 7A-7C, SEM images are provided of a polished magnesium surface, the surface after initial corrosion, and the surface after substantial conversion to yield a corn flake morphology. Referring to FIGS. 8A-8C, corresponding EDX images are provided. The corn flake morphology is formed after 12 hours of immersion in 0.9% PBS solution. Magnesium corrosion is further discussed in Guo et al., Electrochimica Acta 52, 2570 (2007).

Alternatively, the magnesium alloy coating can be treated by a micro-arc surface treatment, e.g., micro-arc oxidation, to form a first tie layer including magnesium oxide and having a defined rough morphology. Micro-arc oxidation is a surface treatment method based on conventional anodic oxidation in a suitable electrolyte by increasing the anodic voltage to a high stage, usually accompanied with gas evolution and sparking phenomena on the anode surface. For example, the magnesium alloy coating is set as an anode and immersed in an aqueous solution of electrolytes including, for example, sodium silicate or sodium hydroxide. In embodiments, a vessel made of, e.g. stainless steel, containing the aqueous solution is set as the cathode. The voltage between the cathode and the anode is controlled to be within the rage of about 100 V to about 200 V. Under the temperature of about 20° C. to 60° C., the anode is immersed for about 20 to about 40 minutes to oxidize the magnesium alloy coating. The oxidized alloy coating includes magnesium oxide and has a defined rough morphology. Micro-arc oxidation is discussed further in T. Qiu et al., Applied Surface Science 253, 3987 (2007).

A selected morphology can also be formed by depositing a biodegradable material on a stent body using glancing angle deposition (GLAD). In some embodiments, brucite, goethite, or lepidocrocite having a surface morphology can be formed on the stent body using GLAD. In particular, brucite nanoneedle or nanorods can be formed by applying an anodization process with an ethanol-water mixture onto the deposited brucite on the stent body.

Figure 10A:
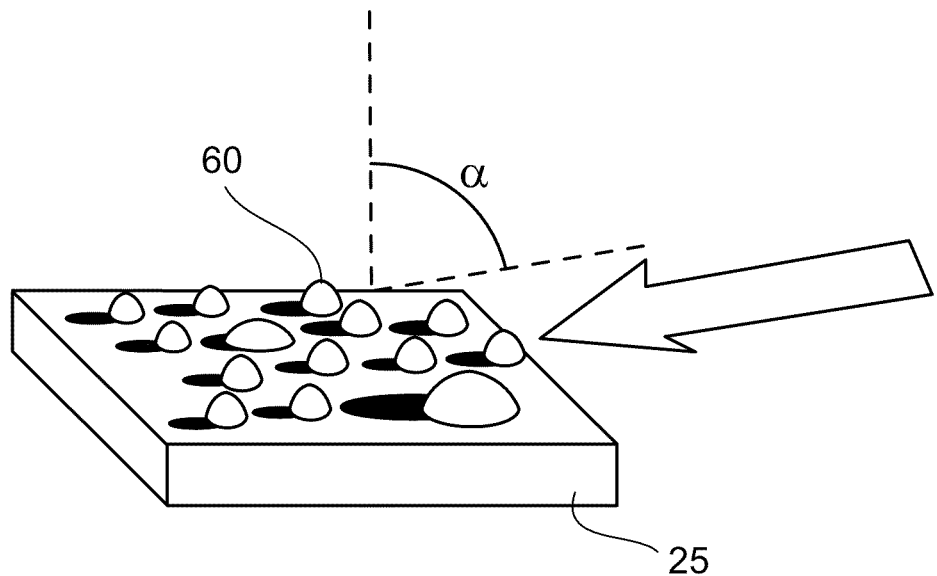
FIGS. 10A-10B are schematic views of a GLAD process.
Like reference symbols in the various drawings indicate like elements.
Figure 10B:
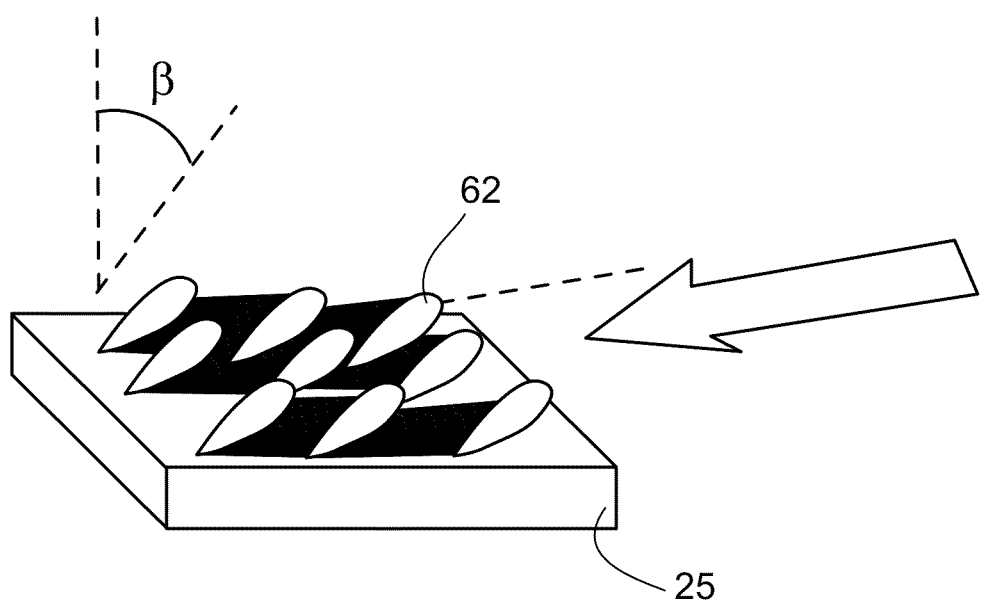

Glancing angle deposition employs oblique angle physical vapor deposition and substrate motion to engineer thin film microstructure on a nanometer scale in three dimensions. Referring particularly to FIG. 10A, a biodegradable material 60, e.g., magnesium, is deposited using GLAD, e.g. physical vapor deposition with the vapor flux arriving at an oblique angle $\alpha$ from the substrate normal. A columnar microstructure is created by deposited material 60, and each column leaves a shadow area that the incident vapor flux does not reach. Referring now to FIG. 10B, first tie layer 62 is formed on stent body 25. The inclined columns in tie layer 62 has a column inclination angle $\beta$. The inclination angle $\beta$ can indicate the porosity of tie layer 62. For example, a larger $\beta$ corresponds to a higher porosity and a smaller β corresponds to a smaller porosity. The inclination angle β, and thus the porosity or the rough morphology, can be tailored by adjusting the vapor incidence angle α and other factors including material and deposition conditions such as substrate and temperature, angular distribution of the deposition flux, background gas pressure and composition, and flux energies. In some embodiments, a larger vapor incident angle α produces a larger inclination angle β, and generally, inclination angle β is smaller than the corresponding incident angle α. In other embodiments, GLAD can be applied to a stent body that has motion, for example, a rotating stent body. The motion of the stent body can facilitate creating morphologies other than columnar within the first tie layer. In some embodiments, a combination of different substrate motions can be used to form the first tie layer with desired morphology. The GLAD technique is described further in k. Robbie et al., J. Vac. Sci Tech. B 16.3, May/June 1998, p. 1115; Vacuum Technology and Coating; and U.S. Ser. No. 12/429,411, filed on Apr. 24, 2009.

In particular embodiments, porous material with a nano-needle morphology can be fabricated by first adding complex dispersants aqueous solution of gelation and lauryl sodium sulfate in the weight ratio of 1:1 to the magnesium aqueous solution in pores 38. Next, an ammonia water solution is injected and stirred for about one hour at a temperature under about 2° C., followed by adding a sodium hydroxide aqueous solution and stirring for another about two hours at a temperature under about 2° C. The mixture is further stirred for one hour, and then heated to and maintained at about 40° C. for two hours before cooling to room temperature. After filtering and washing, the final product is dried for twenty-four hours at 80° C., to produce magnesium hydroxide with a nano-needle morphology. Dispersion is described in Zhang et al., "Surface treatment of magnesium hydroxide to improve its dispersion in organic phase by the ultrasonic technique", Applied Surface Science, Vol. 253, pp. 7393-7397, 2007.

In some embodiments, the material having a morphology can be prepared using wet precipitation. Examples of wet precipitation is described in Lv et al., "Controlled growth of three morphological structures of magnesium hydroxide nanoparticles by wet precipitation method", Journal of Crystal Growth, Vol. 267, pp. 676-684, 2004.

In other embodiments, porous material with a nano-rod morphology can be obtained under similar conditions as the preparation of magnesium hydroxide with a nano-needle morphology described above, except that a higher reaction temperature and a slower injection rate are required. For example, magnesium hydroxide with a nano-rod morphology can be obtained at 10° C. with ammonia water solution injected for three hours, followed by injection of sodium hydroxide aqueous solution for four hours.

Figure 9A:
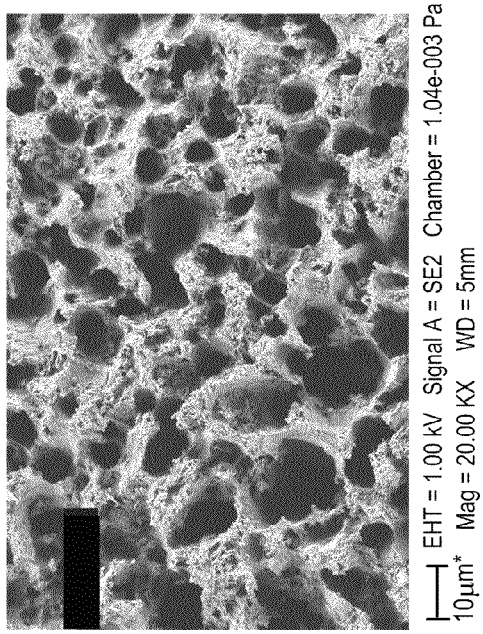
FIGS. 9A-9H are SEM plots and waveforms
Figure 9A:
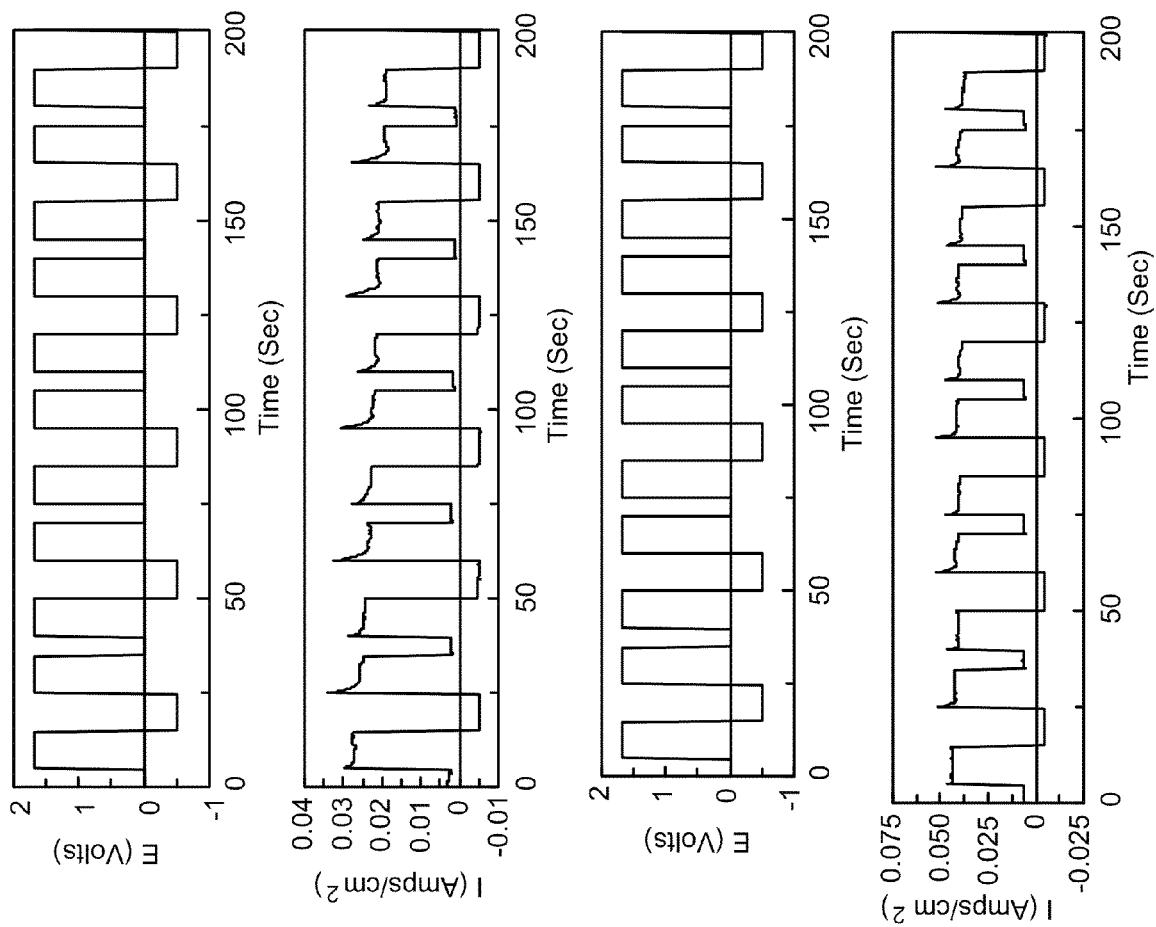
Figure 9B:
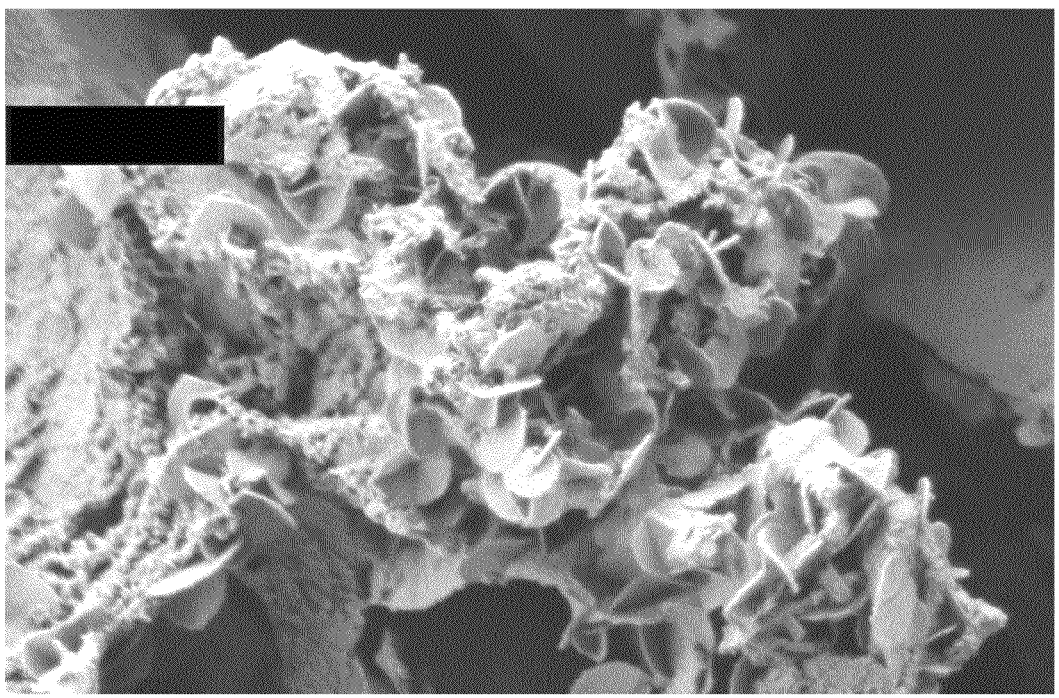
Figure 9B:
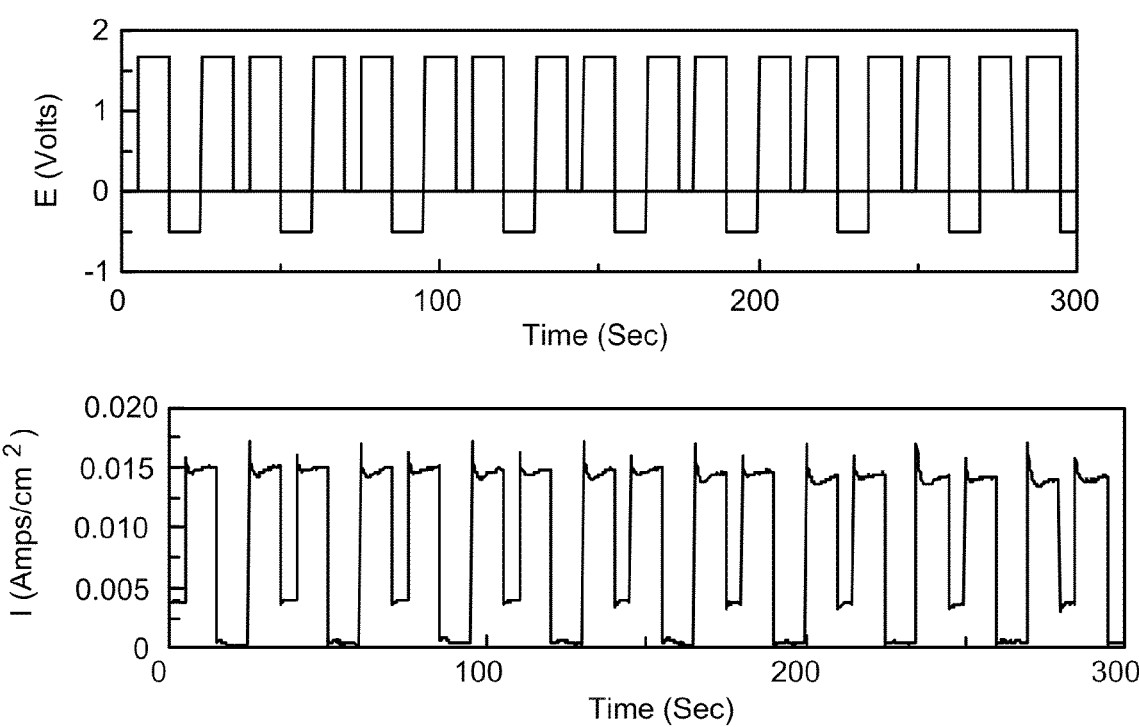
Figure 9C:
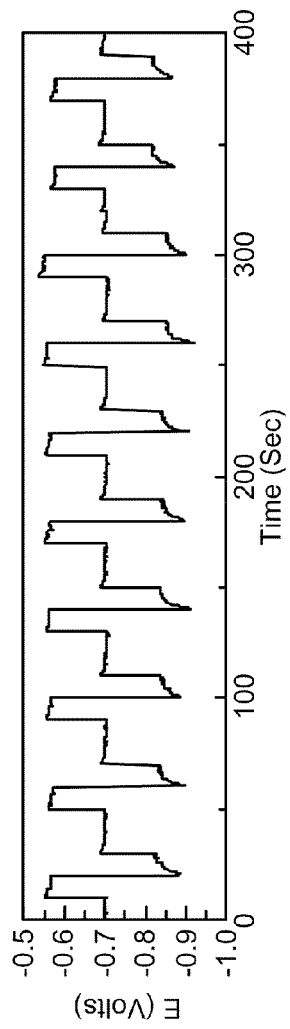
Figure 9C:
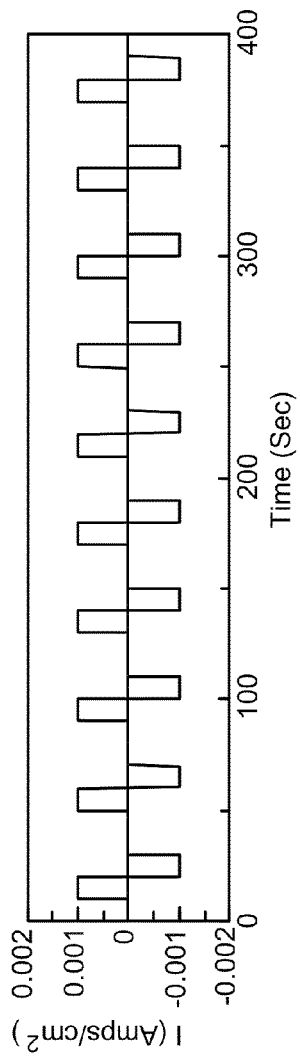
Figure 9C:
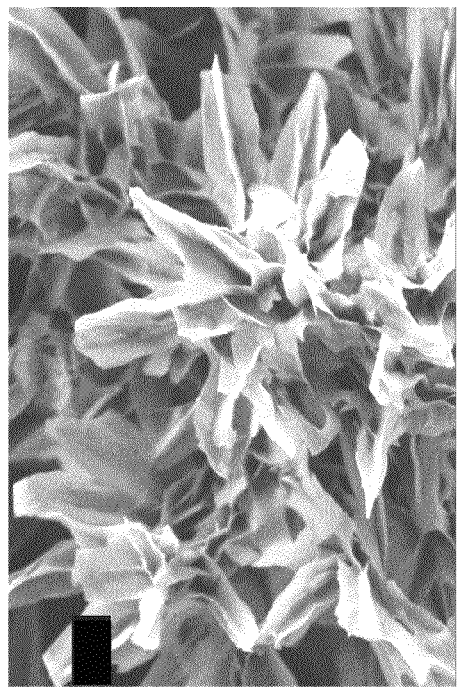
Figure 9C:
Figure 9D:
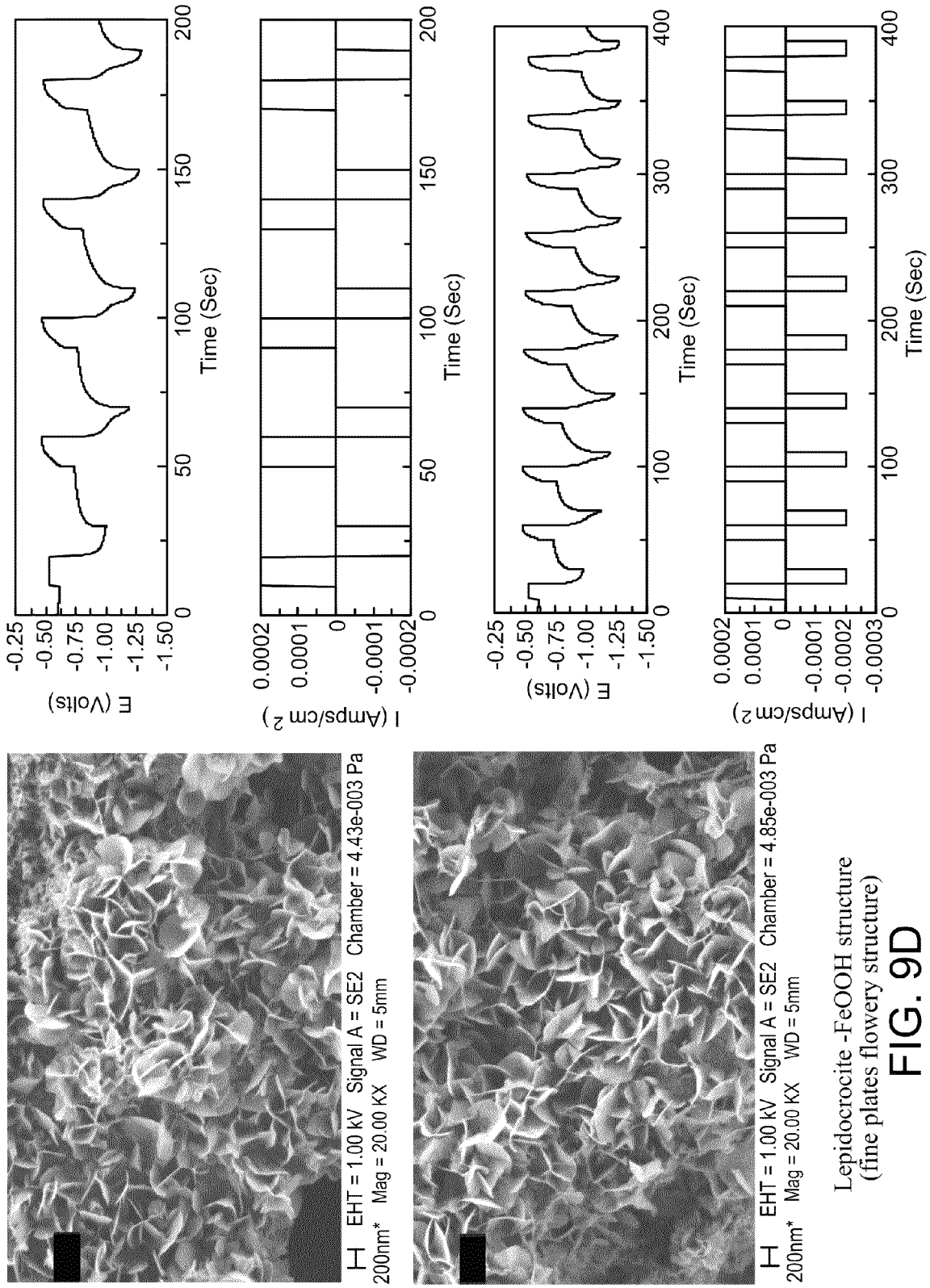
Figure 9E:
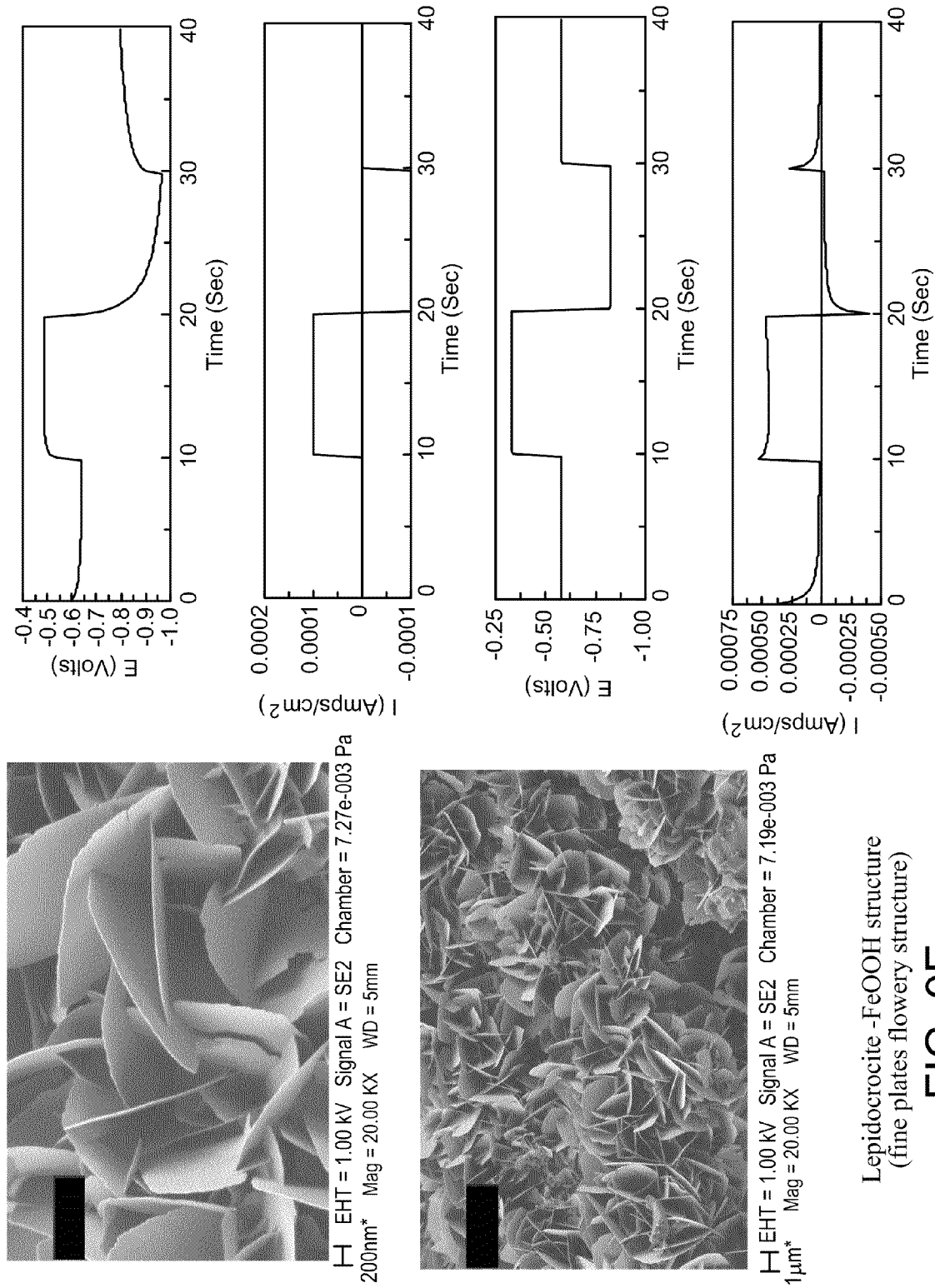
Figure 9F:
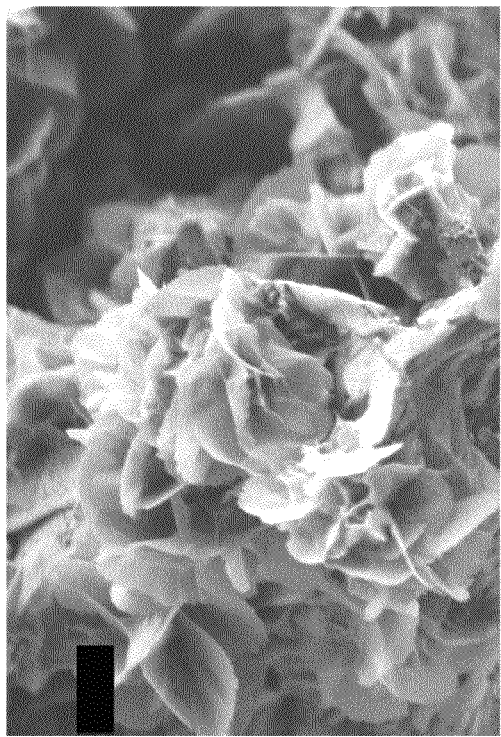
Figure 9F:
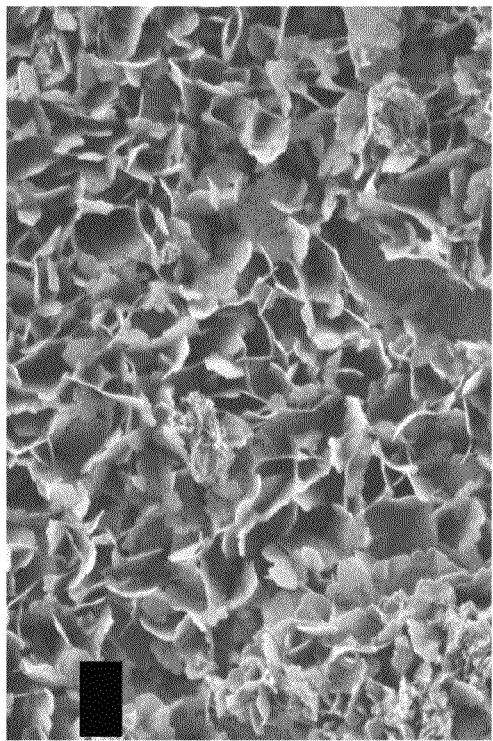
Figure 9F:
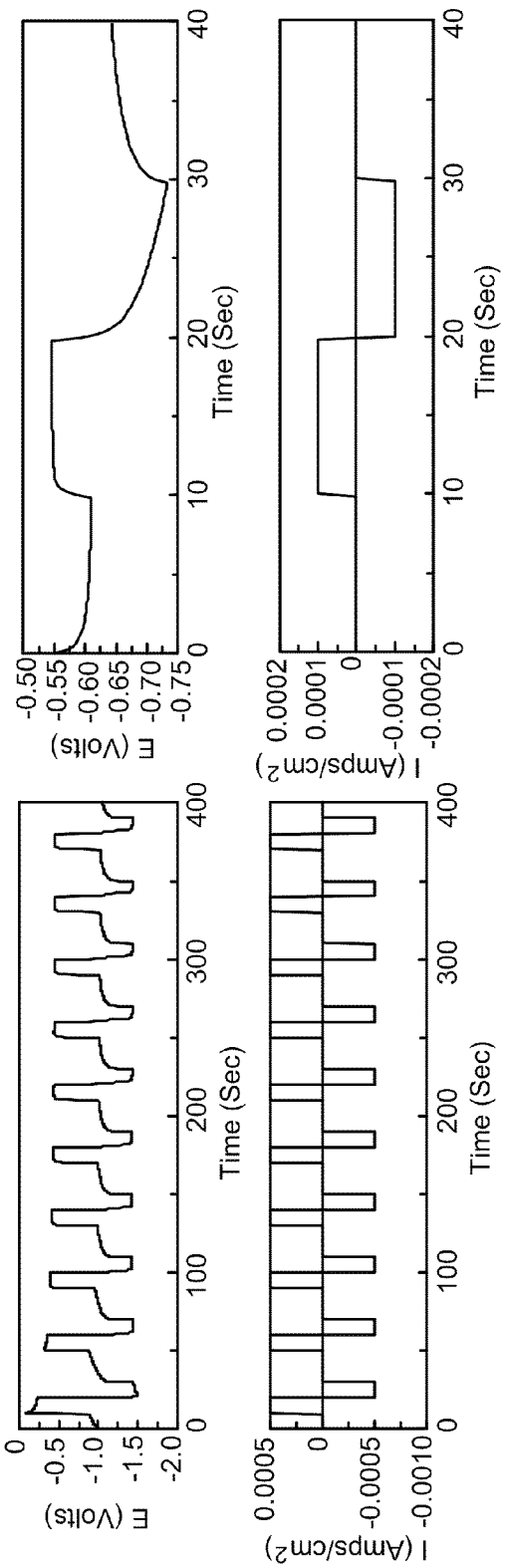
Figure 9G:
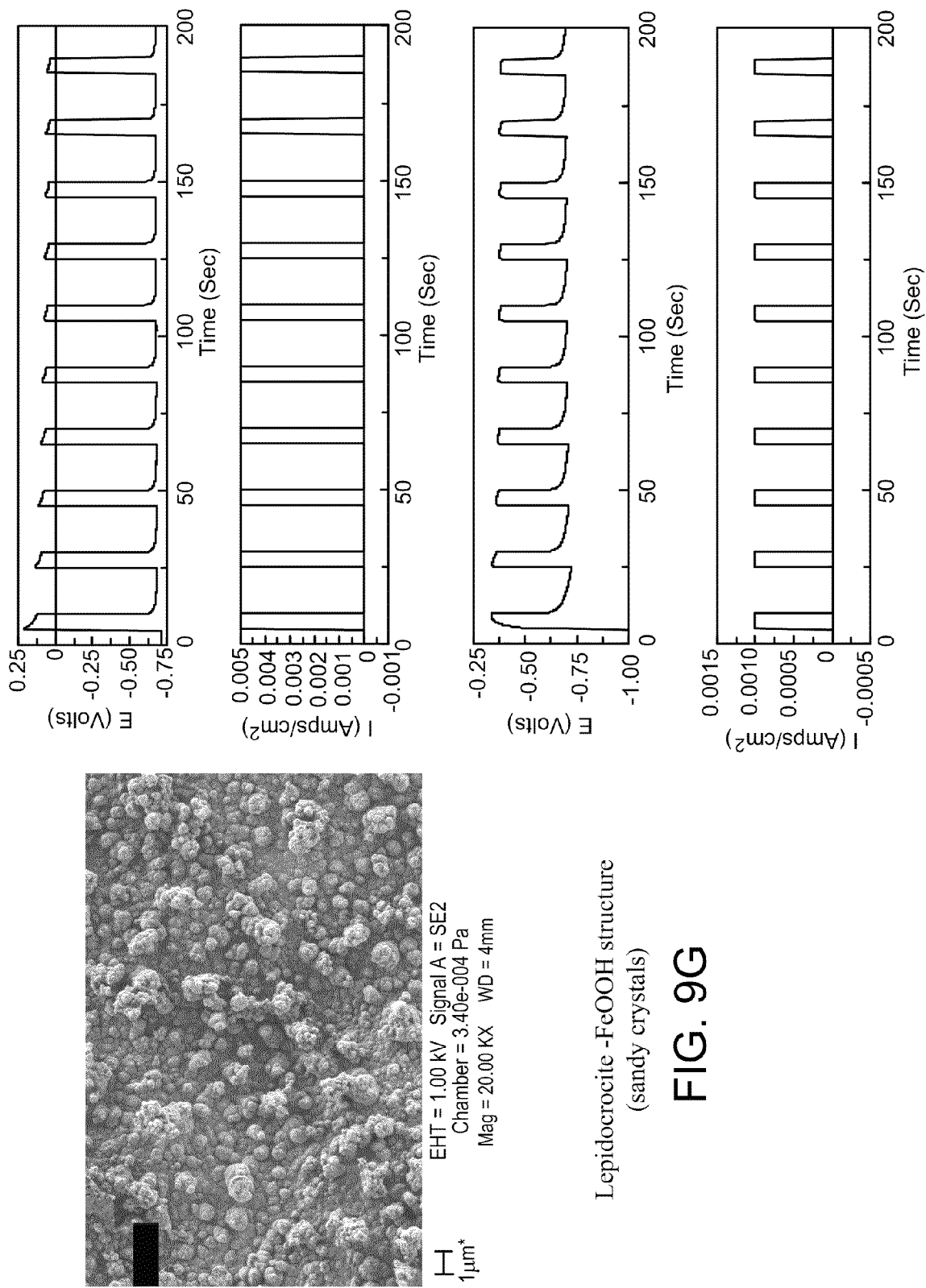
Figure 9H:
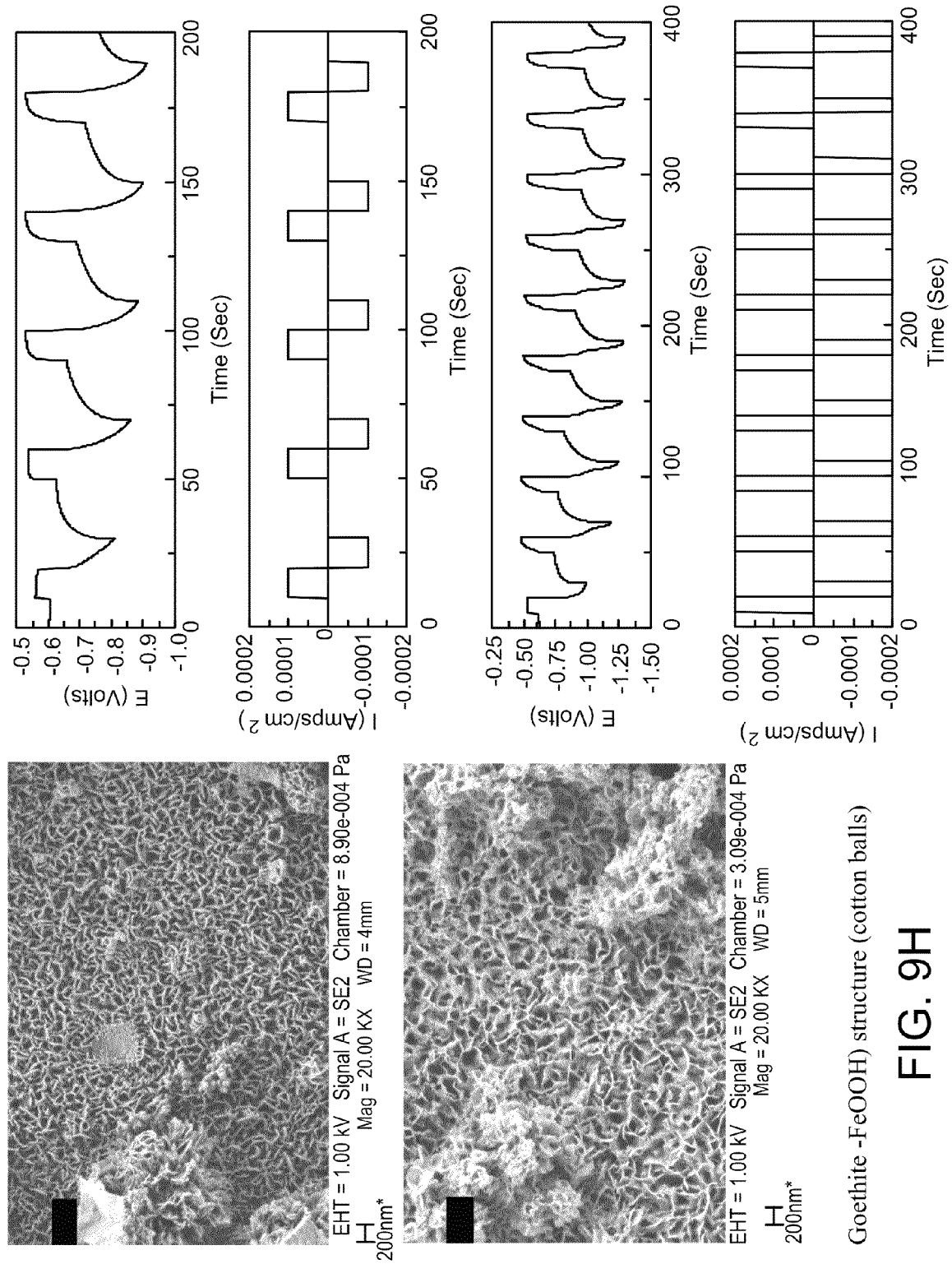

The tie layer can also include iron. The iron can be corroded to provide various morphologies. Referring to FIGS. 9A-9H, electrochemical galvanic and potential square wave treatments for obtaining various iron, iron oxide, or other iron containing morphologies are provided. In particular, ion or ion containing materials are placed in a solution containing sulfuric acid and PBS. Different waveforms are applied, and together with control of other parameters, various iron materials having micro or nano morphologies are formed. Referring to FIG. 9A, iron having features shown in the SEM image is produced using the waveforms shown. Referring to FIG. 9B, hematite α-$Fe_2O_3$ platelet structure is formed using the waveforms shown. Referring to FIGS. 9C and 9F, different lepidocrocite γ-FeOOH structures, e.g., having various fine plates or flowery features, are formed using the waveforms shown. Referring to FIG. 9G, lepidocrocite γ-FeOOH structure having sandy crystals features is formed using the waveforms shown. Referring to FIG. 9H, Goethite γ-FeOOH structure, e.g., having cotton ball features, is formed using the waveforms shown.

Control of morphological structure in magnesium, magnesium oxides or iron, iron oxides, is further described in application Ser. No. 13/069,961 filed Mar. 23, 2011 (US-2011-0238153-A1), filed contemporaneously herewith, Yan et al., Nanotechnology 15, 1625 (2004), Lv et al., Nanotechnology 15, 1576 (2004), and Guo et al., Electrochimica Acta 52, 2570 (2007). Brucite microstructures are also described in Kogure et al., "Microstructure of nemalite, fibrous iron-bearing brucite", Mineralogical Journal, Vol. 20, No. 3, pp. 127-133, July 1998; Liebling et al., "Optical Properties of Fibrous Brucite from Asbestos, Quebec", American Mineralogist, Vol. 57, pp. 857-864, 1972; Buster et al., "Crystal Habits of the Magnesium Hydroxide Mineral Bructite Within Coral Skeletons", poster, 2006; and Hahn et al., "A novel approach for the formation of Mg(OH)2/MgO nanowhiskers on magnesium: Rapid anodization in chloride containing solutions", Electrochemistry Communications, Vol. 10, pp. 288-292, 2008. Corrosion of metals is also described in Matijević, "Colloid Chemical Aspects of Corrosion of Metals", Pure & Appl. Chem., Vol. 52, pp. 1179-1193, 1980 and Antunes et al., "Characterization of Corrosion Products Formed on Steels in The First Months of Atmospheric Exposure", Materia, Vol. 8, No. 1, pp. 27-34, 2003. Electrodeposition is described in Zou et al., "Highly textural lamellar mesostructured magnesium hydroxide via a cathodic electrodeposition process", Materials Letters, Vol. 61, pp. 1990-1993, 2007; Park et al., "Cathodic electrodeposition of RuO2 thin films from Ru(III) Cl3 solution", Materials Chemistry and Physics, Vol. 87, pp. 59-66, 2004; and Lee et al., "A study on electrophoretic deposition of Ni nanoparticles on pitted Ni alloy 600 with surface fractality", Journal of Colloid and Interface Science, Vol. 308, pp. 413-420, 2007. Descriptions of coating morphology and method of making are also provided in Yang et al., "Solution phase synthesis of magnesium hydroxide sulfate hydrate nanoribbons", Nanotechology, Vol. 15, pp. 1625-1627, 2004; Guo et al. "Investigation of corrosion behaviors of Mg-6Gd-3Y-0.4Zr alloy in NaCl aqueous solutions", Electrochemica Acta, Vol. 52, pp. 2570-2579, 2007; Mobedi et al., "Studying the Degradation of Poly(L-lactide) in Presence of Magnesium Hydroxide", Iranian Polymer Journal, Vol. 15, No. 1, pp. 31-39, 2006; Li et al., "A novel method for preparing surface-modified Mg(OH)2 nanocrystallines", Materials Science and Engineering A 452-453, pp. 302-305, 2007; Lv et al., "In situ synthesis of nanolamellas of hydrophobic magnesium hydroxide", Colloids and Surfaces A: Physiochem. Eng. Aspects, Vol. 296, pp. 97-103, 2007; Lv et al., "Controlled growth of three morphological structures of magnesium hydroxide nanoparticles by wet precipitation method", Journal of Crystal Growth, Vol. 267, pp. 676-684, 2004; Lv et al., "Controlled synthesis of magnesium hydroxide nanoparticles with different morphological structures and related properties in flame retardant ethyolene-vinyl acetate blends", Nanotechnology, Vol. 15, pp. 1576-1581, 2004; and Shibli et al., "Development of phosphate inter layered hydroxyapatite coating for stainless steel implants", Applied Surface Science, Vol. 254, pp. 4103-4110, 2008.

In still other embodiments, morphologies other than nano-needle or nano-rod can be prepared by varying conditions of preparation such as reaction temperature and/or reaction speed. Suitable tie layer materials include, for example, magnesium, magnesium alloy, iron, iron alloy, magnesium oxide, or magnesium hydroxide. In some embodiments, a sol gel coating, e.g. MgO—CaO—FeO—ZnO—TaO or manganese oxide, can be formed on top of nano-structured porous material 36 in pores 38 (not shown in figures). The coating can, e.g., stabilize the formed morphologies. Other coatings or methods can also be used. For example, cathodic electrodeposition for oxide formation and sol-electrophoresis can be used. Phosphate coatings that can be formed by wet chemistry and/or nitride coatings formed by cathodic electrodeposition or chemical/physical vapor deposition. The formed morphologies can also be stabilized using colloidal stabilization. Examples of colloidal stabilization is described in Studart et al., "Colloidal Stabilization of Nanoparticles in Concentrated Suspensions", Langmuir, Vol. 23, pp. 1081-1090, 2007.

Referring again to FIG. 3B, polymer coating 32 has a thickness $T_{32}$, and tie layer 30 has a thickness $T_{30}$. In some embodiments, $T_{32}$ is about 100 nm to about 2 microns (e.g., about 300 nm to about 2 microns or about 500 nm to about 2 microns). In embodiments, $T_{30}$ is about 50 nm to about 1 micron (e.g., about 100 nm to about 1 micron or about 200 nm to about 1 micron). In some embodiments, polymer layer includes a biodegradable polymer. For example, polymer layer includes poly(lactic-co-glycolic acid) (PLGA), Polylactic acid (PLA), or Polycaprolactone (PCL). Biodegradable coating is also described in Lakshmi et al., "Biodegradable polymers as biomaterials", Prog. Polym. Sci. Vol. 32, pp. 762-798, 2007. As discussed above, the tie layer can be disposed directly on a stent body that has a biocompatible surface, e.g. a metal such as stainless steel. In embodiments, the tie layer is provided as a layer over the stent body, e.g., a metal such as a radiopaque metal or a ceramic. Suitable ceramics include iridium oxides, which can have a desired morphology, e.g. a rice grain or orange peel type as described in U.S. patent application Ser. No. 11/752,735, filed May 23, 2007 and U.S. patent application Ser. No. 11/752,772, filed May 23, 2007. As discussed above, the tie layer can be coated with another layer to enhance adhesion of a polymer by covalent bonding or hydrogen bond interactions. The coating can be a polymer, ceramic or metal. In embodiments, the coating includes a biodegradable magnesium hydroxide. Chemical bonding occurs between magnesium hydroxide and biodegradable polymers such as poly-lactic acid. In addition to the chemical bond formation between $Mg(OH)_2$ and lactic acid there is also creation of strong connection between polylactide chains and Mg hydroxyl via hydrogen bonding that results in fortification of polymer strings. Addition of $Mg(OH)_2$ also help the mode of polymer degradation change from bulk type to surface type. Similar interaction and beneficial effect can be obtained on other biodegradable polymers such as poly-glycolic acid, PLGA, or poly-amino acids. Further discussion is provided in Mobedi et al., Iranian Polymer Journal 15(1), (2006) 31. The second coating can also be deposited on the first tie layer using a deposition process, such as physical vapor deposition or electrodeposition. In embodiments, other surfaces of the stent, e.g. the luminal surfaces can be provided with a biodegradable tie layer(s) and/or other layers as described above. The layers on different surfaces can be the same or different.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. In embodiments, the drug can be incorporated within the porous regions in a polymer coating. Polymers for drug elution coatings are also disclosed in U.S. Published Patent Application No. 2005/019265A. A functional molecule, e.g., an organic, drug, polymer, protein, DNA, and similar material can be incorporated into groves, pits, void spaces, and other features of the stent.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, such as stainless steel (e.g., 316 L, BioDur® 108 (UNS S29108), and 304 L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stents described herein can be configured for vascular, e.g., coronary and peripheral vasculature or non-vascular lumens. For example, they can be configured for use in the esophagus or the prostate. Other lumens include biliary lumens, hepatic lumens, pancreatic lumens, urethral lumens. The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

All publications, patents, and patent applications referenced above are hereby incorporated by reference in their entirety.

Other embodiments are in the following claims.

What is claimed is:

1. A method of forming an endoprosthesis, comprising
providing an endoprosthesis preform comprising a biodegradable metal, wherein the biodegradable metal is selected from magnesium or iron or alloys thereof;
corroding the biodegradable metal to form a corroded metallic material having a surface morphology including features having thickness to width ratio of about 8:1, and
coating the corroded metallic material with a polymer to form said endoprosthesis.

2. The method of claim 1 further comprising controlling corrosion by immersing the biodegradable metal in a corrosive solution.

3. The method of claim 2 wherein the corrosive solution is an ionic salt solution.

4. The method of claim 3 wherein the ionic salt is NaCl.

5. The method of claim 2 comprising controlling corrosion by inducing galvanic corrosion.

6. The method of claim 1 comprising controlling corrosion by micro-arc oxidation.

7. The method of claim 1 wherein the polymer is biodegradable.

8. The method of claim 1 wherein the polymer includes a drug.

9. The method of claim 1, wherein the morphology is cornflake morphology.

10. The method of claim 9, wherein the cornflake morphology has a thickness to pore width ratio of about 10:1 or more.

11. The method of claim 9, wherein the cornflake morphology has a thickness of about 200 nm or less and a pore opening of about 100 nm or more.

12. The method of claim 1, wherein the morphology is rice grain morphology.

13. The method of claim 12, wherein the morphology has a width of between about 100 nm and about 200 nm.

14. The method of claim 1, further including a biodegradable drug-containing coating bonded to the biodegradable metallic material.

15. The method of claim 1, wherein the endoprosthesis further comprises an alloy of stainless steel, a nickel-titanium alloy or a cobalt alloy.

* * * * *